United States Patent
Chang et al.

(10) Patent No.: US 12,102,682 B1
(45) Date of Patent: Oct. 1, 2024

(54) INJECTABLE PHOTOTHERMAL HYDROGEL BASED ON MELANIN, PREPARATION METHOD, AND APPLICATION THEREOF

(71) Applicant: OCEAN UNIVERSITY OF CHINA, Shandong (CN)

(72) Inventors: Jing Chang, Qingdao (CN); Lili Guo, Qingdao (CN); Lan Guo, Qingdao (CN); Jishang Sun, Qingdao (CN); Cuiyao Li, Qingdao (CN); Baoqin Han, Qingdao (CN)

(73) Assignee: OCEAN UNIVERSITY OF CHINA, Qingdao (CN)

( * ) Notice: Subject to any disclaimer, the term of this patent is extended or adjusted under 35 U.S.C. 154(b) by 0 days.

(21) Appl. No.: 18/593,842

(22) Filed: Mar. 1, 2024

(30) Foreign Application Priority Data

Jul. 21, 2023 (CN) .......................... 202310904416.5

(51) Int. Cl.
| | | |
|---|---|---|
| A61K 41/00 | (2020.01) | |
| A61K 9/00 | (2006.01) | |
| A61K 31/704 | (2006.01) | |
| A61K 47/10 | (2017.01) | |
| A61K 47/22 | (2006.01) | |
| A61K 47/36 | (2006.01) | |

(52) U.S. Cl.
CPC ........ *A61K 41/0057* (2013.01); *A61K 9/0019* (2013.01); *A61K 31/704* (2013.01); *A61K 47/10* (2013.01); *A61K 47/22* (2013.01); *A61K 47/36* (2013.01)

(58) Field of Classification Search
None
See application file for complete search history.

(56) References Cited

U.S. PATENT DOCUMENTS

2011/0230562 A1  9/2011  Holmes et al.

FOREIGN PATENT DOCUMENTS

| CN | 105031665 | | 11/2015 |
|---|---|---|---|
| CN | 105963278 | A | 9/2016 |
| CN | 109044963 | B | 9/2019 |
| CN | 110384654 | B | 4/2022 |
| CN | 115887647 | A | 4/2023 |
| CN | 116059360 | | 5/2023 |
| CN | 116077715 | A | 5/2023 |
| CN | 116139073 | | 5/2023 |
| WO | 2017061673 | A1 | 4/2017 |

OTHER PUBLICATIONS

Notification to Grant Patent Right for Invention in Chinese Application No. 202310904416.5 mailed on Jan. 4, 2024, 4 pages.
First Office Action in Chinese Application No. 202310904416.5 mailed on Dec. 1, 2023, 15 pages.
Min Ah Kim et al., Melanin—PEG Nanoparticles as a Photothermal Agent for Tumor Therapy, Materials Today Communications, 2020, 8 pages.

*Primary Examiner* — Samantha L Shterengarts
*Assistant Examiner* — Jed A Kucharczk
(74) *Attorney, Agent, or Firm* — PORUS IP LLC

(57) ABSTRACT

Embodiments of the present disclosure provide an injectable photothermal hydrogel based on melanin and a preparation method and an application thereof. The injectable photothermal hydrogel is a hydroxypropyl chitosan/bis-amino polyethylene glycol modified melanin nanoparticles (HPCS/MP) hydrogel. The HPCS/MP hydrogel is prepared by mixing bis-amino polyethylene glycol modified melanin nanoparticles (MP) with hydroxypropyl chitosan (HPCS). The MP is synthesized by an amidation reaction of the melanin and the bis-amino PEG. A ratio of a volume of an MP solution to a volume of an HPCS solution in the HPCS/MP hydrogel is 4:6. A concentration of the MP solution is 20 wt %. A concentration of the HPCS solution is 4 wt %.

6 Claims, 23 Drawing Sheets

INJECTABLE PHOTOTHERMAL HYDROGEL BASED ON MELANIN, PREPARATION METHOD, AND APPLICATION THEREOF

CROSS-REFERENCE TO RELATED APPLICATIONS

This application claims priority to Chinese Patent Application No. 202310904416.5, filed on Jul. 21, 2023, the contents of which are hereby incorporated by reference.

TECHNICAL FIELD

The present disclosure relates to the field of hydrogel preparation technology, and in particular to an injectable photothermal hydrogel based on melanin, a preparation method, and an application thereof.

BACKGROUND

In recent years, with the development of multidisciplinary fields of hydrogel research and the gradual maturation of biotechnology, the application fields of the hydrogel are expanding rapidly, and the hydrogel has been used to develop biosensors, contact lenses, wound dressings, etc., in the fields of biomedicine, tissue engineering. Among various stimulus-responsive hydrogels, near-infrared (NIR) light-triggered thermo-responsive hydrogels, i.e., photothermal hydrogels, have gained considerable attention due to the deep-tissue penetration, micro-invasiveness, and temporally and spatially controllable drug release.

In some emerging cancer treatments, photothermal therapy (PTT) is a method of ablating tumor tissues with thermal damage through the use of photothermal agents (PTAs) absorbing NIR light and converting the NIR light into heat, which has high research value due to the simple operation, short treatment time, fast recovery, less invasiveness, and precise spatio-temporal selectivity.

SUMMARY

One or more embodiments of the present disclosure provide an injectable photothermal hydrogel based on melanin. The injectable photothermal hydrogel may be a hydroxypropyl chitosan/bis-amino polyethylene glycol modified melanin nanoparticles (HPCS/MP) hydrogel. The HPCS/MP hydrogel may be prepared by mixing bis-amino polyethylene glycol modified melanin nanoparticles (MP) with hydroxypropyl chitosan (HPCS). The MP may be synthesized by an amidation reaction of melanin and bis-amino PEG. A ratio of a volume of an MP solution to a volume of an HPCS solution in the HPCS/MP hydrogel may be 4:6. A concentration of the MP solution may be 20 wt %. A concentration of the HPCS solution may be 4 wt %.

One or more embodiments of the present disclosure provide a preparation method of the injectable photothermal hydrogel based on the melanin, comprising the following steps:

(1) preparing the MP, including steps of: dissolving $NH_2$-PEG-$NH_2$ in a Tris buffer solution; ultrasonically dispersing melanin in the Tris buffer solution, then adding 1-(3-dimethylaminopropyl)-3-ethylcarbodiimide hydro (EDC) and N-hydroxysuccinimide (NHS), and stirring; dropwise adding a $NH_2$-PEG-$NH_2$ solution into a melanin solution and stirring to obtain a mixed reaction solution; and dehydrating and removing impurities from the mixed reaction solution with absolute ethanol, and freeze-drying to obtain the MP;

(2) preparing the HPCS, including steps of: adding chitosan powder into a NaOH solution to fully swell the chitosan, and removing an excess alkaline solution with suction filtration after freezing; then adding isopropyl alcohol into the chitosan after suction filtration, stirring, adding propylene oxide, and heating in a water bath for reaction; removing an excess reagent of a product with suction filtration, rinsing a filter cake several times with anhydrous ethanol, and then dissolving in deionized water to adjust a pH to neutral; and obtaining the HPCS after dialysis and freeze-drying;

(3) separately weighing MP and HPCS powders and adding distilled water to prepare a 20% (w/v) MP solution and a 4% (w/v) HPCS solution; and (4) evenly mixing the MP solution and the HPCS solution to obtain the HPCS/MP hydrogel.

One or more embodiments of the present disclosure provide an application of the injectable photothermal hydrogel based on the melanin in preparation of a drug carrier.

BRIEF DESCRIPTION OF THE DRAWINGS

The present disclosure is further illustrating by way of exemplary embodiments, which is describing in detail with reference to the accompanying drawings. These embodiments are not limiting, and in these embodiments, the same numbering denotes the same structure, wherein.

DETAILED DESCRIPTION

Figure 1:
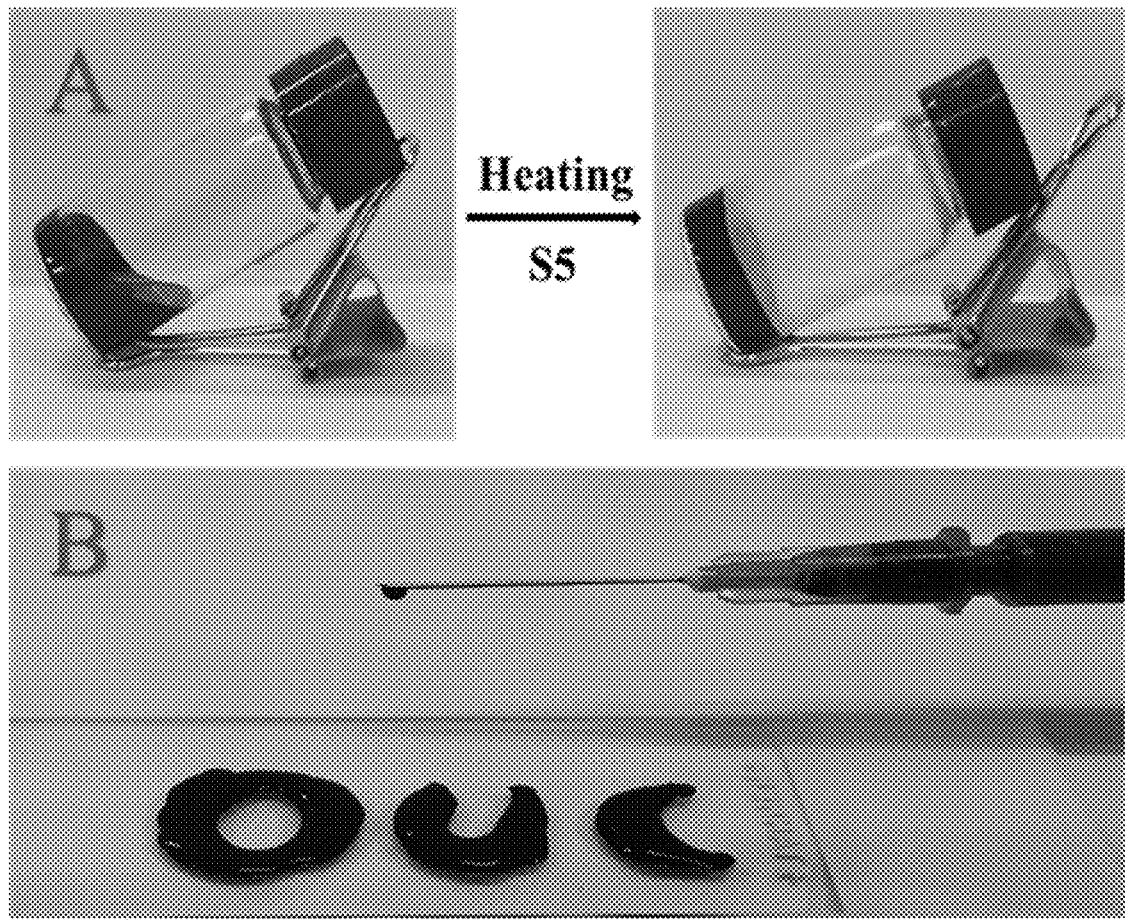
FIG. 1 is a schematic diagram illustrating gel formation and an injectability of a hydrogel according to some embodiments of the present disclosure; wherein A is a schematic diagram illustrating gel formation of an S5 hydrogel, and B is a diagram illustrating a test of an injectability of the hydrogel.

To more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It should be understood that "system", "device", "unit" and/or "module" as used herein is a manner used to distinguish different components, elements, parts, sections, or assemblies at different levels. However, if other words serve the same purpose, the words may be replaced by other expressions.

As shown in the present disclosure and claims, the words "one", "a", "a kind" and/or "the" are not especially singular but may include the plural unless the context expressly suggests otherwise. In general, the terms "comprise," "comprises," "comprising," "include," "includes," and/or "including" merely prompt to include operations and elements that have been clearly identified, and these operations and elements do not constitute an exclusive listing. The methods or devices may also include other operations or elements.

The flowcharts used in the present disclosure illustrate operations that systems implement according to some embodiments of the present disclosure. It should be understood that the previous or subsequent operations may not be accurately implemented in order. Instead, each step may be processed in reverse order or simultaneously. Meanwhile, other operations may also be added to these processes, or a certain step or several steps may be removed from these processes.

The embodiments of the present disclosure provide an injectable photothermal hydrogel based on melanin. The injectable photothermal hydrogel may be a hydroxypropyl chitosan/bis-amino polyethylene glycol modified melanin nanoparticles (HPCS/MP) hydrogel. The HPCS/MP hydrogel may be prepared by mixing bis-amino polyethylene glycol modified melanin nanoparticles (MP) with hydroxypropyl chitosan (HPCS).

Hydrogel is a gel with water as a dispersing medium, which is a polymer network system, soft in nature, and capable of keeping a certain shape and absorbing a large amount of water. As a kind of a high water absorption and high water retention material, hydrogel is capable of being used as a mask in cosmetics, an antipyretic patch, an analgesic patch, a drug carrier in medicine, etc.

The photothermal hydrogel is a type of thermo-responsive hydrogel triggered by NIR light, with deep tissue penetration, micro-invasiveness, and controlled release of drugs. A release rate of a drug-carrying photothermal hydrogel may be adjusted by adjusting parameters such as light wavelength, power density, exposure time, and beam diameter.

The injectable hydrogel has advantages over conventional hydrogels such as good biocompatibility, ease preparation, targeting property, and efficient loading of nanomedicines. The injectable hydrogel may be configured to efficiently carry drug by mixing with the drug in a solution status and forming an in-situ hydrogel at a target site after injection.

The injectable photothermal hydrogel is a hydrogel that combines the characteristics of the photothermal hydrogel and the injectable hydrogel.

The MP is synthesized by an amidation reaction of the melanin and the bis-amino PEG.

In some embodiments, a ratio of a volume of an MP solution to a volume of an HPCS solution in the HPCS/MP hydrogel may be within a range of 7:3-3:7, 7:3-4:6, 7:3-5:5, 3:7-4:6, or 3:7-6:4, or the like.

In some embodiments, the ratio of the volume of the MP solution to the volume of the HPCS solution in the HPCS/MP hydrogel may be 7:3, 6.5:3.5, 6:4, 5.5:4.5, 5:5, 4:6, or 3:7, or the like.

In some embodiments, the ratio of the volume of the MP solution to the volume of the HPCS solution in the HPCS/MP hydrogel may be 4:6, i.e., a concentration of the MP solution may be 20 wt %, and a concentration of the HPCS solution may be 4 wt %. The HPCS/MP hydrogel may have a relatively tight surface structure, relatively good mechanical strength, and suitable void structure favorable for encapsulation and slow release of the drug under the solution ratio. More descriptions may be found in the related descriptions of Example 2.

The natural melanin is a heterogeneous polymer formed by 5,6-dihydroxyindole-2-carboxylic acid (DHICA) and 5,6-dihydroxyindole (DHI) at a preset ratio. The preset ratio may be within a range of 6:4-8.5:1.5, such as 6:4, 7:3, 8:2, or the like. Due to a highly conjugated structure of the melanin, the melanin has good light absorption effect, which is capable of absorbing light within a range from a NIR light to a visible light, to convert a light energy into a heat energy, thereby reflecting a good photothermal conversion effect.

In some embodiments, the HPCS/MP hydrogel may have the tight surface structure. The void structure of the HPCS/MP hydrogel may satisfy preset void requirements. The preset void requirements may be set artificially. For example, the void structure of the HPCS/MP hydrogel may be 30-60% of a total volume of the hydrogel, such as 30%, 40%, 50%, 60%, etc. A hydrogel bond cross-linking reaction is formed within hydrogel molecules of the HPCS/MP hydrogel, such that the HPCS/MP hydrogel is injectable.

In some embodiments, the HPCS/MP hydrogel may maintain a stability at 37° C. or a gelation temperature of 43° C. An encapsulation efficiency of the HPCS/MP hydrogel may be 90%+3%. An encapsulated drug from the HPCS/MP hydrogel may be more conducive to be released under an acidic environment (e.g., under an environment of a pH less than 5.7). A controlled release of the encapsulated drug from the HPCS/MP hydrogel may be achieved through an external laser.

The embodiments of the present disclosure provide a preparation method of the injectable photothermal hydrogel based on the melanin, comprising the following steps:

(1) preparing the MP, including steps of: dissolving $NH_2$-PEG-$NH_2$ in a Tris buffer solution; ultrasonically dispersing the melanin in the Tris buffer solution, then adding 1-(3-dimethylaminopropyl)-3-ethylcarbodiimide hydro (EDC) and N-hydroxysuccinimide (NHS), and stirring; dropwise adding a $NH_2$-PEG-$NH_2$ solution into a melanin solution and stirring to obtain a mixed reaction solution; and dehydrating and removing impurities from the mixed reaction solution with absolute ethanol, and freeze-drying to obtain the MP;

(2) preparing the HPCS, including steps of: adding chitosan powder into a NaOH solution to fully swell the chitosan, and removing an excess alkaline solution with suction filtration after freezing; then adding isopropyl alcohol into the chitosan after suction filtration, stirring, adding propylene oxide, and heating in a water bath for reaction; removing an excess reagent of a product with suction filtration, rinsing a filter cake several times with anhydrous ethanol, and then dissolving in deionized water to adjust a pH to neutral; and obtaining the HPCS after dialysis and freeze-drying;

(3) preparing an MP solution and an HPCS solution, including steps of: separately weighing MP and HPCS powders and adding distilled water to prepare a 20% (w/v) MP solution and a 4% (w/v) HPCS solution; and;

(4) evenly mixing the MP solution and the HPCS solution to obtain the HPCS/MP hydrogel. More descriptions regarding the preparation method of the injectable photothermal hydrogel based on the melanin may be found in Example 1 and related descriptions thereof.

In some embodiments, the melanin in the step (1) may be natural melanin, and the melanin may be extracted from cuttlefish.

The embodiments of the present disclosure provide an application of the injectable photothermal hydrogel based on the melanin in preparation of a drug carrier. The drug carrier is a system capable of altering a manner in which a drug enters a human body and a distribution of the drug in the human body, and delivering the drug directionally to a target organ. The hydrogel has a low mobility, and can stay at a specific site for a long time to realize the effect of slow release of the drug. The hydrogel has good biocompatibility and biodegradability, and can maintain or control a release of encapsulated hydrogel drug to a body fluid, which is a good drug carrier. The injectable photothermal hydrogel drug carrier for drug delivery is capable of effectively control the release of the drug and reduce damage to an organism. The HPCS/MP hydrogel of the encapsulated drug may be injected through a syringe, activated in vivo, and irradiated to release the drug by an infrared light.

In some embodiments, an application of the HPCS/MP hydrogel in preparation of a drugs suitable for photothermal treatment is provided. The photothermal treatment refers to a manner of light radiation for disease treatment, utilizing certain drugs that change in response to exposure to a specific light. The HPCS/MP hydrogel may be used as a drug carrier in the photothermal treatment to carry a plurality of drugs simultaneously to achieve combined treatment.

In some embodiments, an application of the HPCS/MP hydrogel in preparation of an anti-cancer drug is provided. The HPCS/MP hydrogel may be used as a carrier of the anti-cancer drug to deliver the drug to a tumor site to release based on a change in a temperature and pH of a tumor microenvironment.

The HPCS/MP hydrogel prepared in the embodiments of the present disclosure have good temperature responsiveness, injectability, biodegradability, and biosafety. The photothermal performance studies show that the HPCS/MP hydrogel has high photothermal conversion efficiency and photothermal stability and a high drug-carrying encapsulation rate (approximately 90%); and a drug release of the HPCS/MP hydrogel has a typical pH sensitivity and exogenous laser controllability. More descriptions may be found in the related descriptions of Example 2 and Example 3.

The photothermal property of the HPCS/MP hydrogel combined with the drug exerts excellent results without toxic and side effects.

The technical solutions described herein are further described and illustrated in the following in combination with embodiments.

Example 1

A preparation method of an HPCS/MP hydrogel may comprise the following steps.
1. Melanin was extracted.
   (1) A cuttlefish ink sac was removed to obtain ink, and the ink was washed with water and ethanol several times to obtain an initial extract of cuttlefish melanin.
   (2) The initial extract of the melanin was soaked in deionized water for 24 h, and then centrifuged at 14000 rpm for 30 min to obtain a precipitate, a large amount of deionized water was added into the precipitate, and a pH of the precipitate was adjusted to 10.5 with a 0.2 mol/L NaOH solution; then alkaline protease with a mass fraction of 1.5% was added into the precipitate, and enzymolysis was carried out in a water bath at 50° C. for 4 h for enzyme inactivation; and finally the precipitate was obtained by centrifugation at 14000 rpm for 20-30 min, the precipitate was washed to neutral with the deionized water, and then freeze-dried to obtain purified cuttlefish melanin. The purified cuttlefish melanin was packed into vacuum sealed bags and stored in a refrigerator at 4° C. away from light.
2. The MP was prepared.
   (1) 0.15 g (0.002 M) of $NH_2$-PEG-$NH_2$ was dissolved in 15 mL (0.01 g/mL) Tris buffer solution (pH=9).
   (2) 0.33 g (0.001 M) of the melanin was placed in 66 mL (0.005 g/mL) of the Tris buffer solution, and ultrasonically dispersed for 20 min, then 0.31 g (0.002 M) of EDC and 0.23 g (0.002 M) NHS were added into the solution and stirred magnetically for 2 h, and a dissolved PEG solution was dropwise added into the melanin solution and stirred for 12 h; a reaction mixture was poured into 5 times the volume of anhydrous ethanol and centrifuged for 20 min at 14000 rpm at a room temperature, a supernatant was discarded, a precipitate was collected, and then the precipitate was washed with the anhydrous ethanol for 3 times, and then freeze-dried to obtain the MP product.
3. The HPCS was prepared.
   (1) 3 g of chitosan was taken and added to 20 mL of 30% NaOH solution and stirred for 1 h at the room temperature to fully swell the chitosan, and then frozen at −40° C. for 24 h, frozen chitosan was thawed, and suction-filtered to remove an excess alkaline solution;
   (2) 40 mL of isopropyl alcohol was added into the chitosan after suction filtration, stirred for 30 min at the room temperature, then 25 mL of propylene oxide was added, and the reaction was heated in a water bath at 50° C. with condensate turned on, and then the reaction was terminated after 6 h.
   (3) An excess reagent was removed by suction filtration, the filter cake was rinsed with anhydrous ethanol for several times and then dissolved in the deionized water; a pH value was adjusted to neutral; and the HPCS was obtained after dialysis and freeze-drying, and was ground to powder.
4. The HPCS/MP hydrogel was prepared.
   A certain mass of MP and HPCS powders were weighed separately, and distilled water was added to prepare an MP solution with a concentration of 20% (w/v) and a HPCS solution with a concentration of 4% (w/v). The prepared MP solution and HPCS solution were mixed based on volume ratios of 7:3, 6.5:3.5, 6:4, 5.5:4.5, 5:5, 4:6, and 3:7, respectively, to obtain seven hydrogels with different HPCS/MP ratios.

Example 2

Measurement and analysis were performed on the HPCS/MP hydrogels prepared in Example 1.
1. A gelatinization temperature was determined using a test tube inversion method.
2. Morphologies of the HPCS/MP hydrogels were observed.

The prepared HPCS/MP hydrogels were freeze-dried, sprayed with gold for 200 s, and surface structures of the HPCS/MP hydrogels were observed under SEM at 15 kv of an acceleration voltage.

3. Fourier infrared spectra of the HPCS/MP hydrogels were determined.

The prepared HPCS/MP hydrogels were freeze-dried, ground into powder to be mixed with dried potassium bromide at a mass ratio of 1:100, milled homogeneously, and pressed into a homogeneous and transparent sheet, which was placed in a Fourier infrared spectrometer to perform infrared spectral scanning.

4. Rheological properties of the HPCS/MP hydrogels were determined.

The hydrodynamic properties of the HPCS/MP hydrogel samples were tested using a rotational rheometer.

5. Photothermal conversion properties and photothermal stabilities of the HPCS/MP hydrogels were studied.

0.5 mL of a hydrogel solution of each of the seven ratios of HPCS/MP based on Example 1 was taken, and irradiated for 10 min using a NIR laser of 808 nm at an optical density of 1.0 W/cm$^2$, to ensure that laser spots cover the solution; distilled water was irradiated under a same condition to record a temperature change as a blank control. The temperature change was recorded every 10 s using a thermal imager. The operation was repeated three times for each group of samples as parallel data, and an average value of the three groups of data was taken at last. Then, a temperature rise of a same hydrogel system within 10 min irradiation of the NIR laser of 808 nm at four different power densities of 0.5, 1.0, 1.5, and 2.0 W/cm$^2$ was studied, the temperature change was recorded every 10 s using the infrared thermal imager, and the operation was repeated three times for each group of samples. A photothermal stability test was performed using a light on-off cycle experiment. The hydrogel system was irradiated with 808 nm of NIR light at an optical density of 1.0 W/cm$^2$ for 10 min, then the laser was turned off and the system was cooled down at the room temperature, and the temperature change was recorded. Then the above operation was repeated three times, and the data was recorded every 10 s.

The photothermal conversion efficiency of the hydrogel is calculated according to the following equation:

$$\eta = \frac{hs\Delta T_{max} - Q_{dis}}{I(1 - 10^{-A\lambda})}$$

Wherein h denotes a heat transfer coefficient, s denotes a spot area, $\Delta T_{max}$ denotes a maximum temperature difference, $Q_{dis}$ denotes heat (0.02 J/s) absorbed by a solvent, I denotes a laser power, and $A_\lambda$ denotes an absorbance of the sample at 808 nm.

hs is calculated by the following formula:

$$t = \frac{mC_p}{hs}\ln\theta$$

Wherein t denotes a cooling time, θ is $(T-T_{surr})/\Delta T_{max}$, T denotes a photothermal temperature, and $T_{surr}$ denotes an ambient environment. A slope is obtained by fitting t to lnθ to calculate hs. m denotes a mass of the distilled water in the system, and $C_p$ denotes a specific heat capacity of the distilled water.

Results analysis is as follows.

1. Analysis of Gelation Conditions of the HPCS/MP Hydrogel

Over a certain range, as a specific gravity of the MP solution increases, the sample undergoes gelation, and a gelation time and a lowest gelation temperature (LCST) decrease. But beyond the certain range, the MP solution does not have much effect on the gelation of the hydrogel, and the gel time and gel temperature are essentially constant. In view of an uncertainty of a safety issue brought about by a larger concentration of melanin, combined with the results of the characterization of rheology, X-ray Diffraction (XRD), thermogravimetry, and morphology of several hydrogels not subjected to ratio preparation, the hydrogel prepared by mixing the HPCS solution with the concentration of 4% (w/v) with the MP solution with the concentration of 20% (w/v) (i.e., S5 in Table 1) at the volume ratio of 4:6 was selected for subsequent experiments.

TABLE 1

Gelation parameter indices of the HPCS/MP hydrogels with different ratios

|  | HPCS w/v (%) | MP w/v (%) | HPCS/MP (V/V) | Gel formation temperature (° C.) | Gel formation time (min) |
|---|---|---|---|---|---|
| S1 | 4 | 20 | 7:3 | — | — |
| S2 | 4 | 20 | 6:4 | — | — |
| S3 | 4 | 20 | 5:5 | 50 | >20 |
| S4 | 4 | 20 | 5.5:4.5 | 48 | 20 |
| S5 | 4 | 20 | 4:6 | 43 | 15 |
| S6 | 4 | 20 | 3.5:6.5 | 43 | 14 |
| S7 | 4 | 20 | 3:7 | 43 | 14 |

In FIG. 1, (A) illustrates a transformation process of gelation of an S5 hydrogel after heating for 15 min at the temperature of 43° C. The hydrogel presented in a solution status and flowed with tilting of a reagent vial at the room temperature. However, the hydrogel heated after 15 min at 43° C. no longer flowed, and gelation occurred. In FIG. 1, (B) illustrates an injection of the hydrogel via 1 mL of a syringe at the room temperature, which indicates that the HPCS/DOX/MP hydrogel was injectable.

2. Observation of the Morphology of the HPCS/MP Hydrogel

Figure 2:
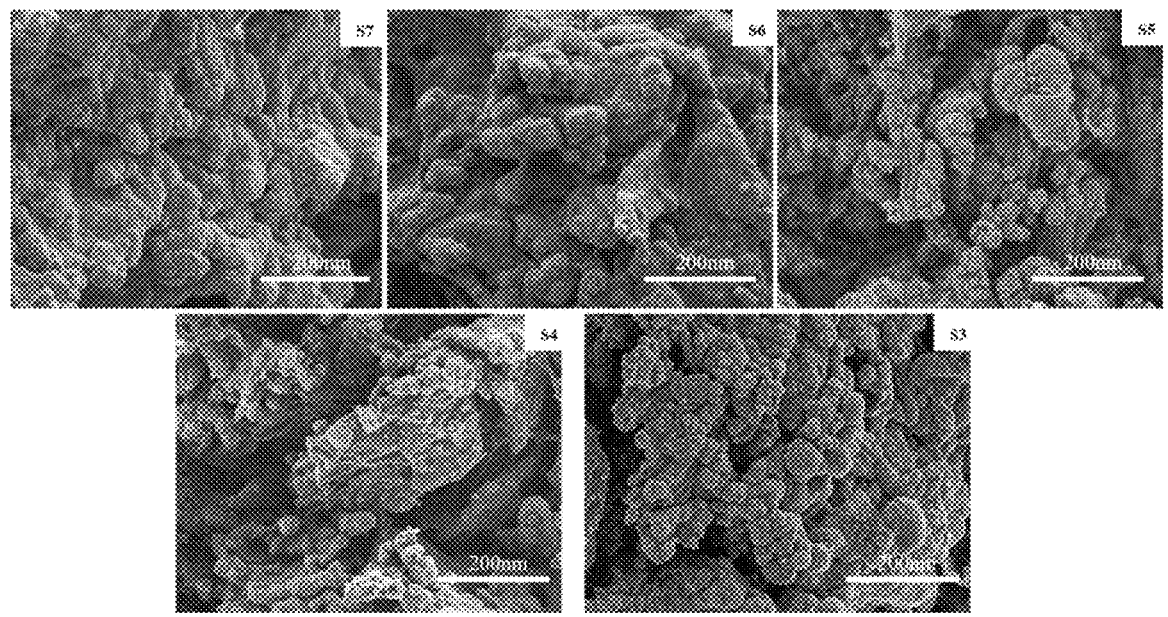
FIG. 2 is scanning electron microscope (SEM) (400×) pictures of surface morphologies of hydrogels with different ratios according to some embodiments of the present disclosure.

As illustrated in FIG. 2, as the specific gravity of the MP increases, a structure of the HPCS/MP hydrogel is tighter, surface voids of the HPCS/MP hydrogel are fewer, and a mechanical strength of the HPCS/MP hydrogel increases. The more loose the structure of the HPCS/MP hydrogel, the less likely the hydrogel is to maintain the structure, which is easily destroyed. The void structure of the hydrogel is configured to better encapsulate and release the drug. However, too many voids lead to a decrease in the mechanical properties of the hydrogel and an inability to control the release of the drug, resulting in a large release within a short period of time after injection into the body. The two hydrogels S3 and S4 had very loose surface structures, which were not tightly arranged, and thus the mechanical strengths of the hydrogels S3 and S4 were poor. The surface structures of the two hydrogels S6 and S7 were very tight, the void structures were almost not observed, and it was very difficult for the encapsulated drug to reach release through the void. Compared with several other samples, S5 had a tighter surface structure, which was capable of guaranteeing a certain degree of mechanical strength, and an appropriate amount of void structures were also conducive to encapsulation and slow release of the drug.

3. Infrared Spectral Analysis of the HPCS/MP Hydrogel

Figure 3:
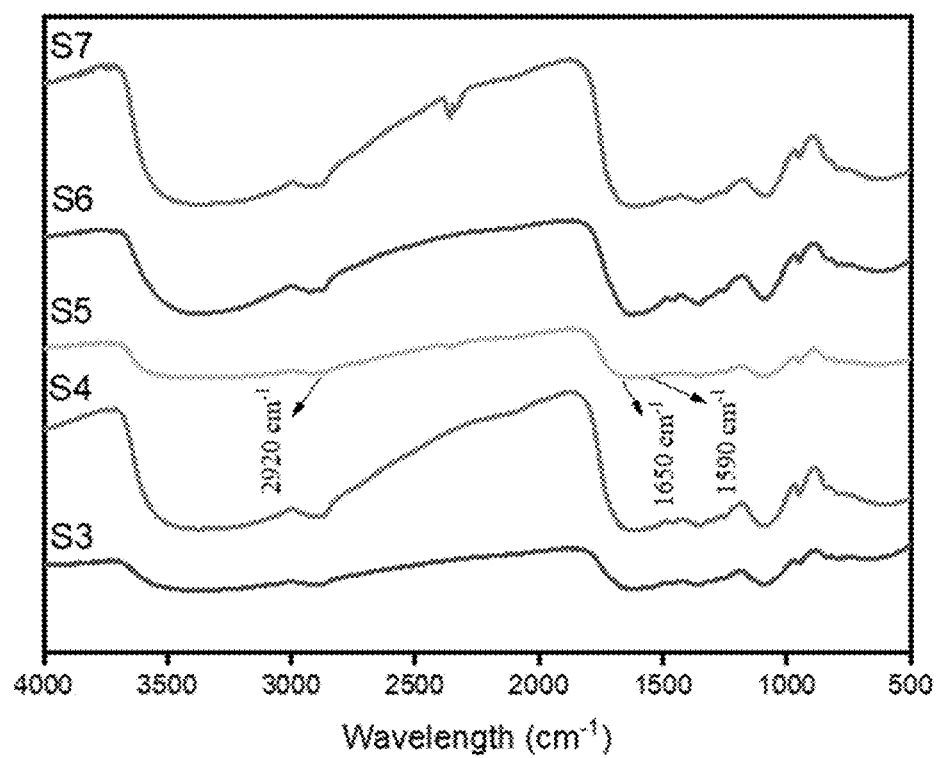
FIG. 3 is a schematic diagram illustrating a Fourier infrared spectrogram of an HPCS/MP hydrogels with different ratios according to some embodiments of the present disclosure.

As illustrated in FIG. 3, characteristic peaks of the HPCS at wavelengths of 1657 $cm^{-1}$ and 1599 $cm^{-1}$ disappeared, and at the same time, characteristic peaks of an amide bond of the HPCS shifted peak images to a lower waveband, and peak intensities were weakened, which indicated that a hydroxyl group in the HPCS structure might form a hydrogen bond with $NH_2$ in the MP structure. Meanwhile, the peak intensities of the infrared spectrum of the HPCS/MP hydrogel at wavelengths of 2900 $cm^{-1}$ and 1062 $cm^{-1}$ were weakened, and a hydrogen bond cross-linking reaction was formed within the hydrogel molecules.

4. Rheological Property Analysis of the HPCS/MP Hydrogel

Figure 4:
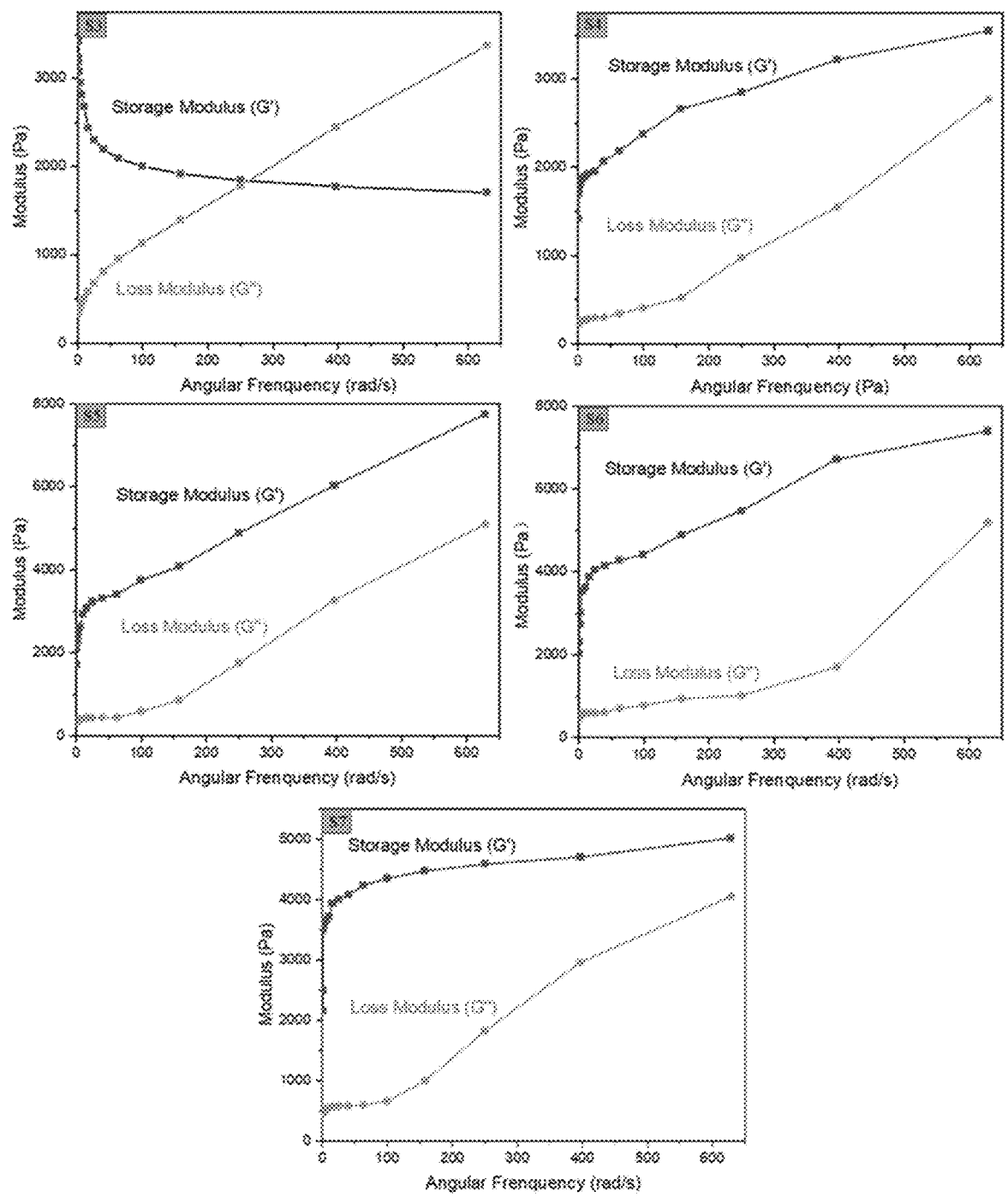
FIG. 4 is schematic diagram illustrating elastic modulus analysis of an HPCS/MP hydrogels with different ratios according to some embodiments of the present disclosure.

As illustrated in FIG. 4, an energy storage modulus (G') was greater than a depletion modulus (G") for all groups of hydrogels except an S3 hydrogel. The fact that G' was greater than G" indicated that at a set room temperature, the hydrogel is capable of maintaining the cross-linked structure all the time with good stability. With acceleration of a scanning frequency, the G' and G" of the hydrogels increased all the time, which indicated that the cross-linking of the prepared hydrogels depends on intermolecular non-covalent interaction rather than covalent bonding interaction. The larger G' and G" of S5 hydrogel compared to S4, S6, and S7 hydrogels, which indicated that the S5 hydrogel had a higher mechanical strength.

Figure 5:
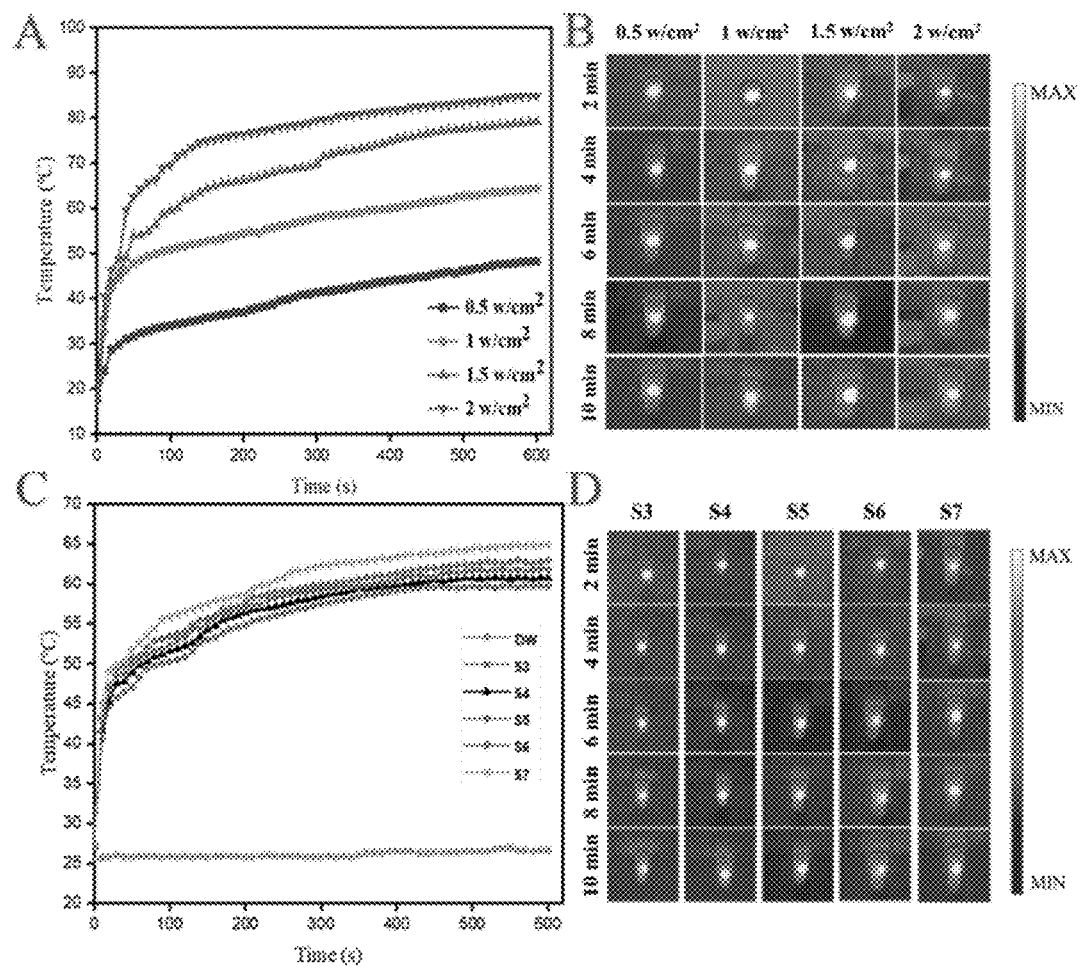
FIG. 5 is a schematic diagram illustrating a heating curve and a thermogram of a hydrogel according to some embodiments of the present disclosure; wherein A is a schematic diagram illustrating heating curves of an S5 hydrogel at different powers, B is a schematic diagram illustrating thermograms of an S5 hydrogel at different powers, C is a schematic diagram illustrating heating curves of hydrogels with different ratios at 1 power of $W/cm^2$, and D is a schematic diagram illustrating thermograms of hydrogels with different ratios at 1 power of $W/cm^2$.

5. Study of the Photothermal Conversion Properties and Stabilities of the HPCS/MP Hydrogels As illustrated in FIG. 5 (C, D), it can be seen that first 4 min of irradiation was a period of rapid temperature rise of the hydrogel. As the proportion of the MP component in the hydrogel system increased, the temperature rise of the hydrogel increased. Compared to the S7 hydrogel, the temperature rise of the S5 hydrogel was not as high. After 5 min of irradiation, the S5 hydrogel was capable of reaching 55° C., achieving a temperature required to ablate tumor cells in a relatively short period of time, and the temperature was not too high to pose certain safety risks. The highest temperature reached within 10 min was about 60° C. Meanwhile, the S5 hydrogel could gelatinize within 3 min of irradiation. In FIG. 5 (A, B), it can be seen that the temperature rise of the hydrogel presented a certain power dependence. From an application perspective, a power of 1.0 $W/cm^2$ was more appropriate compared to several other powers, as a heating curve was smooth, the temperature did not rise too quickly.

Figure 6:
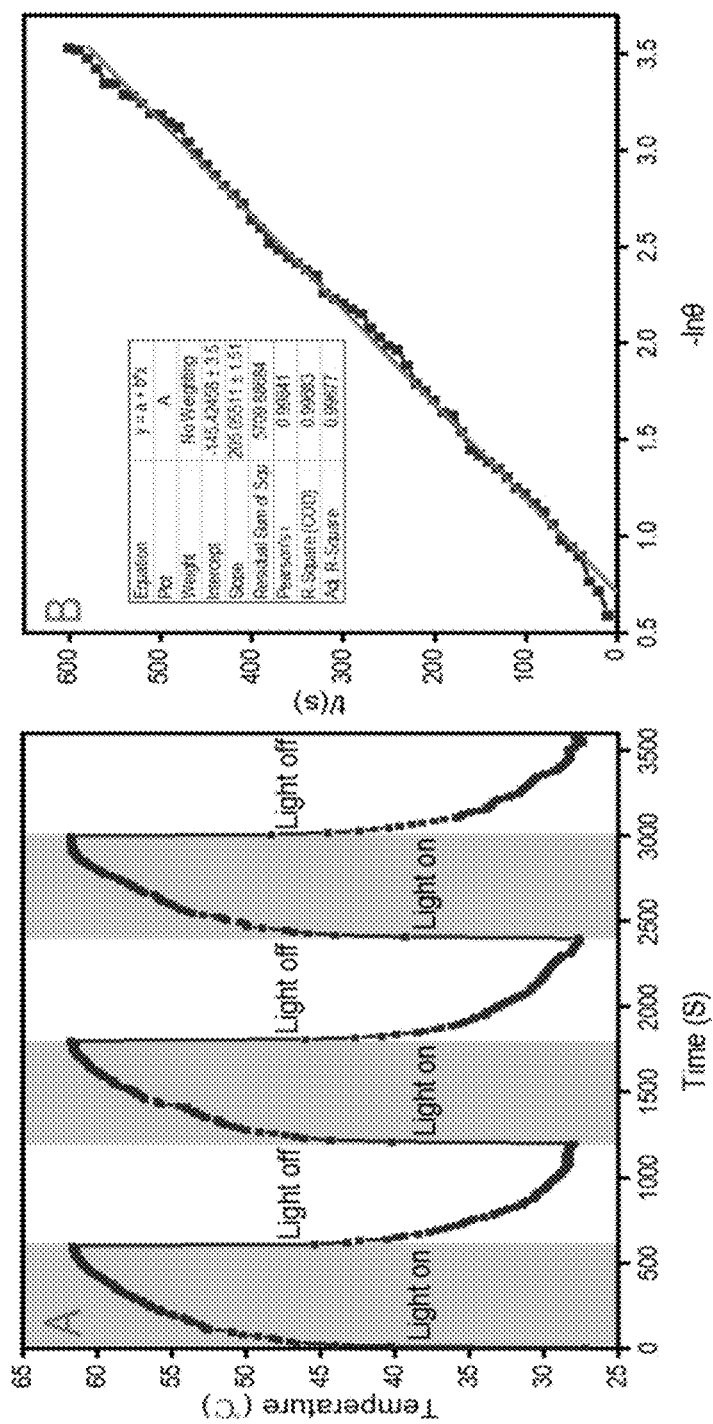
FIG. 6 is a schematic diagram illustrating a photothermal property of an S5 hydrogel according to some embodiments of the present disclosure; wherein A is a schematic diagram illustrating an effect of photothermal stability, and B is a schematic diagram illustrating a linear fitting curve in calculation of photothermal efficiency.

In FIG. 6 (A), it can be seen that while reaching the highest temperature within 10 min, the hydrogel was capable of reducing to an initial temperature within 10 min, thereby avoiding damage to normal tissues or cells of a human body caused by constant high temperature. Based on a slope of a fitting curve in FIG. 6 (B), the photothermal conversion efficiency of the hydrogel was calculated to be approximately 41%, indicating a wide range of application for the hydrogel in photothermal treatment.

Example 3

The Example is directed to experiments on in-vitro application of the hydrogel

1. Drug Carrying and Release of the Hydrogel

50 μg of doxorubicin hydrochloride (DOX·HCL) was dissolved in water and then added dropwise to a MP aqueous solution of 20% (w/v) and stirred for 12 h. A HPCS solution of 4% (w/v) was mixed with the MP aqueous solution of 20% (w/v) at an optimal ratio of 4:6 to prepare a drug-carrying hydrogel. A surface of the hydrogel was gently rinsed with deionized water, and a rinsing solution was collected to measure a fluorescence intensity. An encapsulation efficiency of the doxorubicin hydrochloride was calculated from a plotted standard curve. A hydrogel encapsulation efficiency EE (%) was calculated to be 90%+3%.

100 mg of DOX·HCL-carrying hydrogel was placed in 50 mL of phosphate buffer saline (PBS) of different pH values (pH=5.7 and pH=7.4), respectively. A release rate of the drug-carrying hydrogel in a 37° C. and 100 rpm thermostatic oscillation incubator under conditions of NIR light irradiation and no irradiation, respectively, was studied. A laser irradiation group LASER was irradiated with an NIR laser emitter of 808 nm at a power of 1.0 W/cm$^2$ for 5 min. The irradiation was started from 0th h, and then performed every 24 h to study a relationship between a release of doxorubicin hydrochloride over time.

At each time point of 4, 6, 8, 10, 12, 24, 36, 48, 60, 72, 84, 96, 108, 120, 132, 144, 156, 168, and 180 h during a release process, 200 μL of PBS was pipetted from the system to determine absorbance values at two fluorescence wavelengths of 478 and 596 nm, and 200 μL of fresh PBS was added to ensure a volume of the system to be constant. A cumulative release of DOX·HCL was calculated by a standard curve, and a release curve of DOX·HCL over time was plotted.

Figure 7:
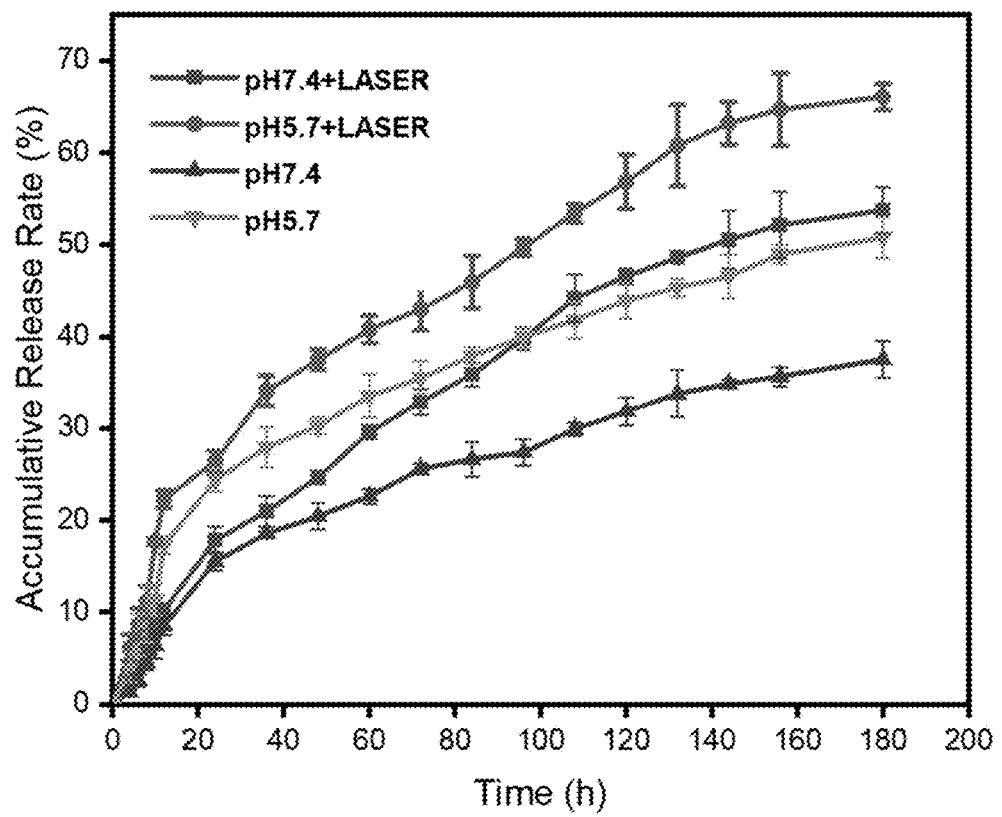
FIG. 7 is a schematic diagram illustrating curves of release of DOX·HCL with NIR light illumination and time at a temperature of 37° C. according to some embodiments of the present disclosure.

As illustrated in FIG. 7, it can be seen that the drug-carrying hydrogel had a faster and higher release rate at pH 5.7 compared to pH 7.4, and similarly, the NIR light irradiation group had a higher release rate than a non-light-irradiation group. After 180 h of release, the release rate of the NIR light irradiation group at pH 5.7 was capable of reaching approximately 65% compared to 50% of the non-light-irradiation group at pH 5.7, with the former being about 1.5 times as high as the latter. The release rate of the NIR light irradiation group at pH 7.4 after 180 h was approximately 55%, while the release rate of the non-light irradiation group was approximately 35%.

The above results indicate that the encapsulated drug from the hydrogel is more conducive to be released under the acidic environment, and the NIR light irradiation improves the release rate within the same time, which can promote the drug from the hydrogel to be released. Controlled release of the drug may be achieved through an external laser.

2. Evaluation of Cytocompatibility of the HPCS/DOX/MP Hydrogel

An in-vitro cellular cytotoxicity of the HPCS/MP hydrogel was tested using a medium immersion method. L929 cells were digested, centrifuged, and diluted to 2×10$^4$ cells/mL, and then seeded in 96-well plates and cultured for 24 h. 100%, 80%, 60%, 40%, 20%, and 10% of hydrogel extract solutions were added, and a positive control group without the extract solution and a blank control group without cells were set up. Then 20 μL of thiazolyl blue (MTT) solution was added to each well and incubated for 4 h away from light and taken out. 180 L of dimethyl sulfoxide (DMSO) solution was added to each well, and an absorbance value of each well was detected using a microplate reader (incubated for 10 min at a wavelength of 492 nm and 37° C.). A relative cell proliferation rate was calculated.

Figure 8:
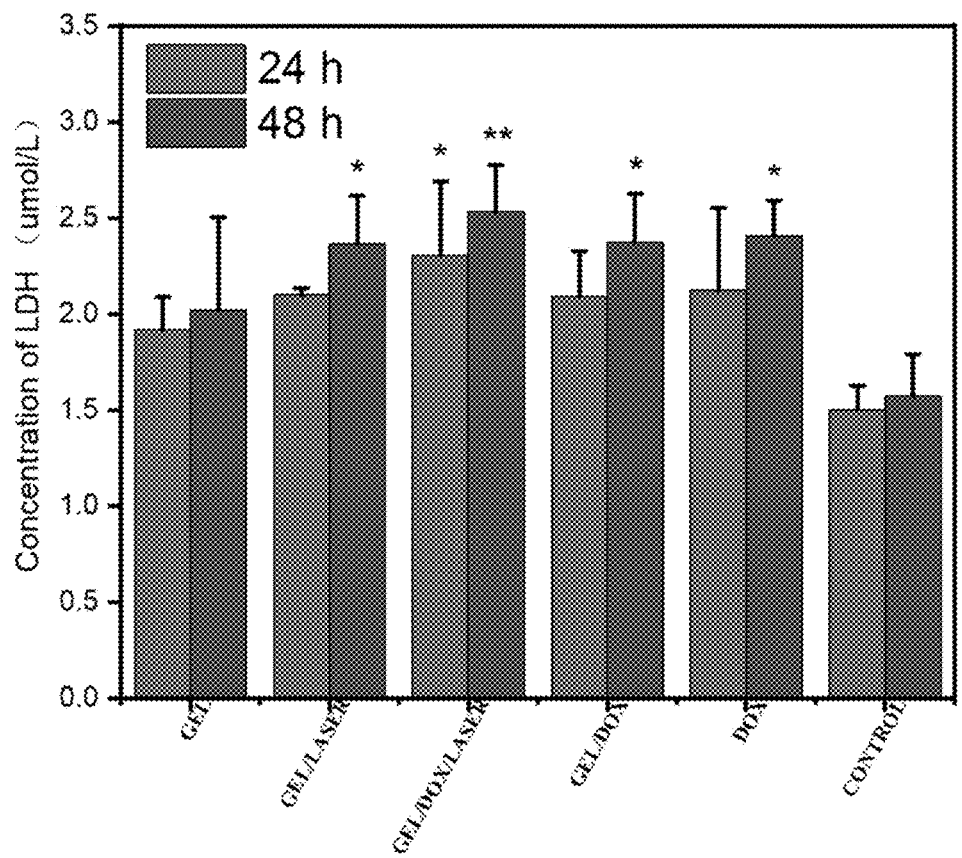
FIG. 8 is a schematic diagram illustrating a relative proliferation rate of L929 cells treated with different concentrations of hydrogel extract solutions at 24 h and 48 h according to some embodiments of the present disclosure.

As illustrated in FIG. 8, it can be seen that all concentrations of the extract solutions were not toxic to the cells.

3. In-Vivo Degradation of the Hydrogel

Eighteen female Sprague-Dawley (SD) rats, with an average body weight of 180 g (4 weeks of age), were randomly divided into 6 groups with 3 rats per group. The HPCS/MP hydrogel was cut into blocks with a volume of approximately 6×6×4 mm$^3$ (mass of approximately 80 mg) and 3×3×2 mm$^3$ (mass of approximately 40 mg) in size and implanted into dorsal subcutaneous and thigh muscles of the rats, respectively. The rats were routinely reared after the operation, and the rats were put to death at time points of 2, 4, 7, 15, 21, and 28 d. Anatomical observations and photographs were taken of the implanted parts of the backs and the legs of the rats, and a degradation of the hydrogels and tissue inflammatory reactions and morphologies of the corresponding parts were recorded.

Figure 9:
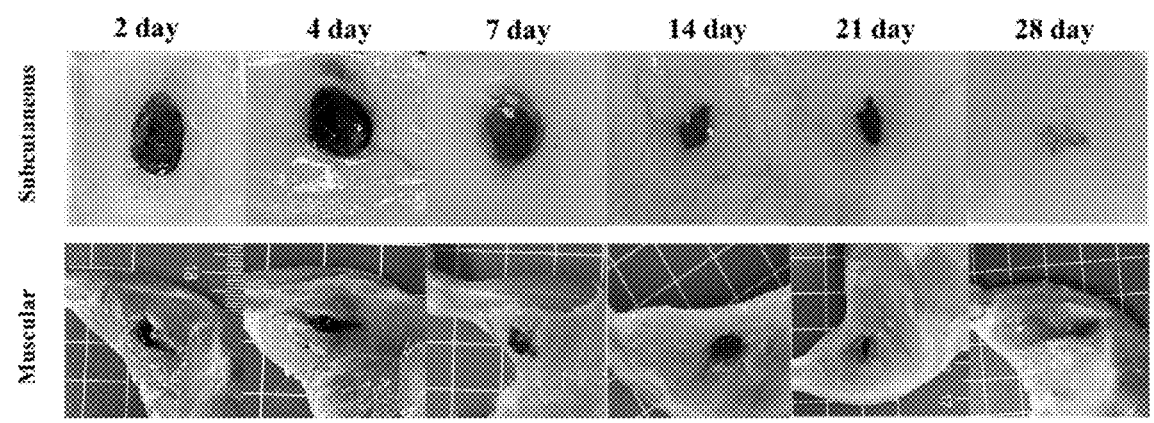
FIG. 9 is a schematic diagram illustrating a degradation of a hydrogel extract solution at different implantation sites according to some embodiments of the present disclosure.

After the surgical implantation, the rats in all groups could eat and behave normally, and no obvious abnormalities were found. As illustrated in FIG. 9, on the 4th day after surgical implantation, the hydrogels were only partially degraded and a slight inflammatory reaction occurred at the implantation sites, with the appearance of red blood and slight swelling in the leg muscle; on the 28th day, the dorsal subcutaneous hydrogels were almost invisible, with only a small amount of hydrogels remained, and most of the hydrogels in the leg muscles was degraded, with no obvious inflammatory reaction.

Figure 10:
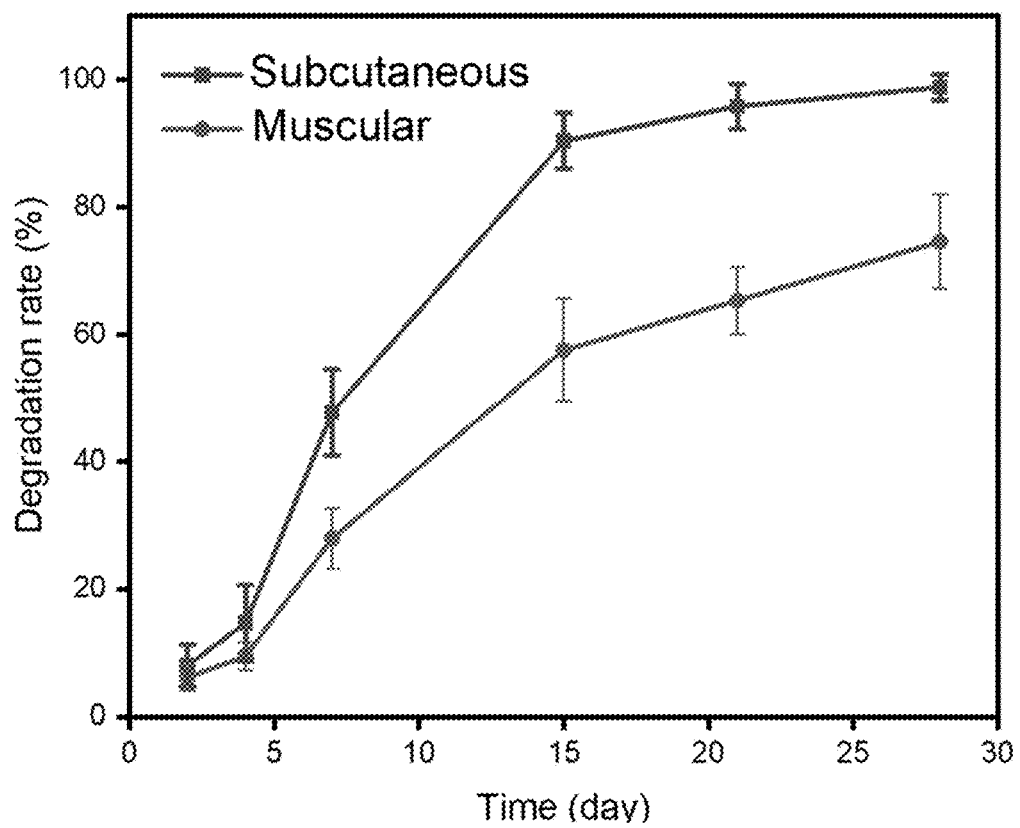
FIG. 10 is a schematic diagram illustrating curves of degradation of a hydrogel with time at two implantation sites according to some embodiments of the present disclosure.

The above results indicate that the in-vivo HPCS/MP hydrogel has good stability within a certain time range. As illustrated in FIG. 10, the hydrogel has a good in-vivo biodegradability with a percentage of subcutaneous degradation close to 100% on the 28th day and approximately 75% in muscles.

Figure 11:
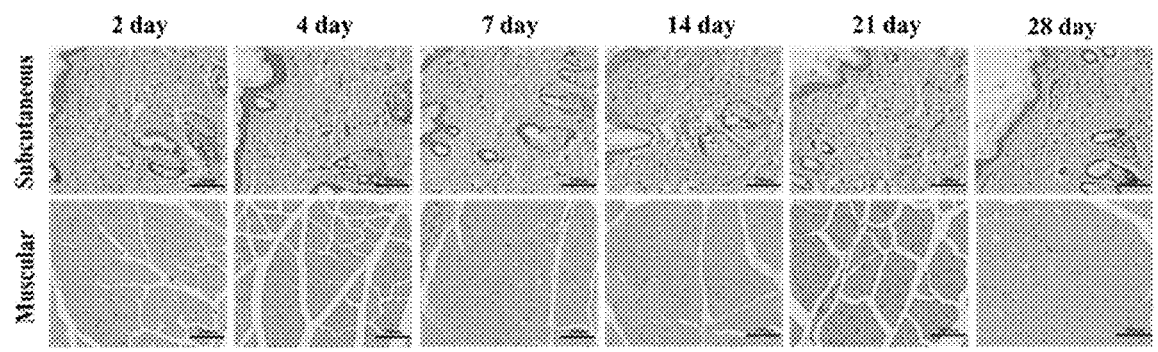
FIG. 11 is a schematic diagram illustrating HE staining (200×; Bar=200 nm) according to some embodiments of the present disclosure.

The dorsal subcutaneous and peri muscular tissues of the legs implanted with the hydrogel were taken out and then sliced and observed by HE staining for pathological analysis. As illustrated in FIG. 11, it can be concluded that inflammatory cells appeared on the 2nd and 4th days after hydrogel implantation in the subcutaneous dorsal area, and the inflammatory cells gradually disappeared with a degradation time, and no abnormality could be observed, thereby indicating good histocompatibility of the HPCS/MP hydrogel.

4. Hemolytic Analysis of the Hydrogel

A certain amount of hydrogel and a sodium chloride injection of 0.9% were added into a prepared hydrogel sample and a sodium chloride solution of 0.9% at a ratio of 0.1 g/mL. A hydrogel extract solution was obtained by incubating for 72 h in a shaker at 37° C. and 100 rpm.

The hydrogel extract solution was mixed with a prepared erythrocyte suspension of 5% at a volume ratio of 1:1, and a solution obtained by mixing deionized water with the erythrocyte suspension at the volume ratio of 1:1 was used as a positive control group, and a solution obtained by mixing a sodium chloride solution of 0.9% with the erythrocyte suspension at the volume ratio of 1:1 was used as a negative control group, which were incubated in an incubator at a constant temperature of 37° C. for 1 h, then centrifuged at 2000 rpm for 5 min, and a supernatant was aspirated. An absorbance value at a wavelength of 540 nm was detected with a microplate reader to calculate the relative hemolysis rate of erythrocytes.

Figure 12:
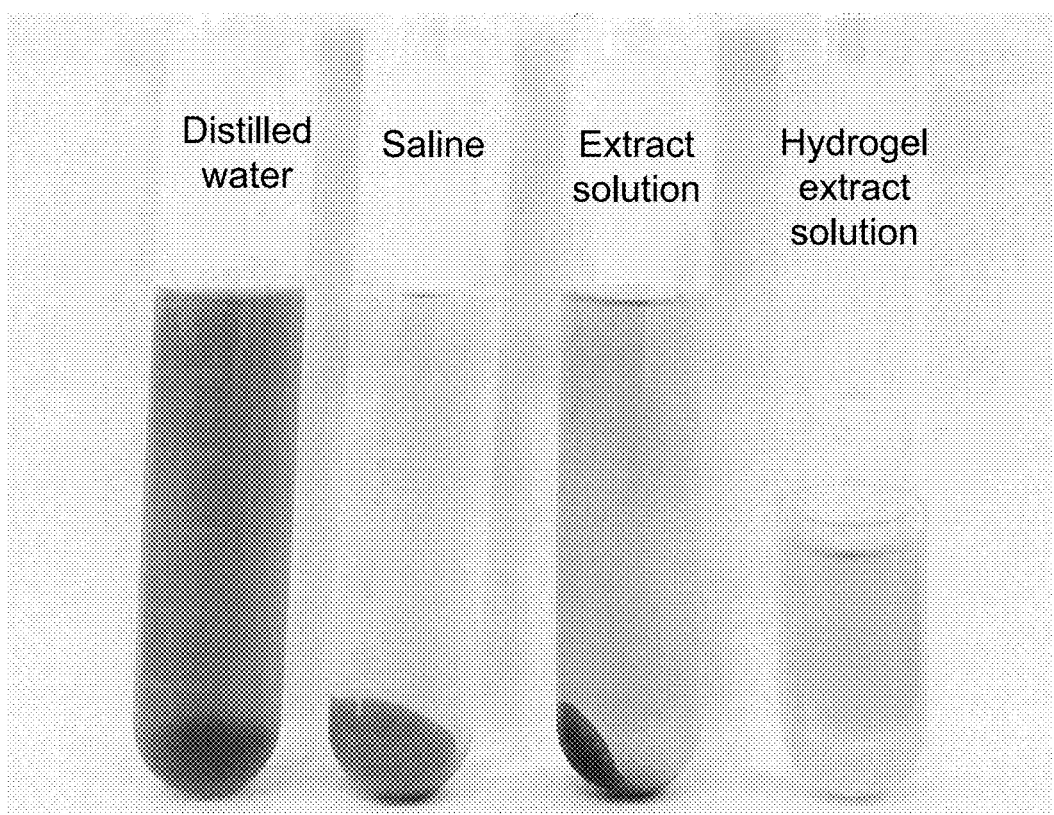
FIG. 12 is a schematic diagram illustrating hemolysis according to some embodiments of the present disclosure.

As illustrated in FIG. 12, it can be seen that the supernatant of both the negative control group and a material group was transparent, and there was basically no release of hemoglobin, and all the erythrocytes remained intact, while the supernatant of the positive control group showed a clear red color, and some of the erythrocytes ruptured and released hemoglobin. A hemolysis rate value was 4.6% after the absorbance value was calculated. The above indicates that the hemolytic toxicity of the hydrogel material is small, and the hydrogel material does not cause obvious hemolytic behavior, and has good biocompatibility.

5. Combined Photothermal-Chemotherapeutic Action Killing A549 Cells

The experiment was divided into 5 groups: 1) a Control group: no drug effect; 2) a GEL group: addition of the HPCS/MP hydrogel; 3) a GEL/LASER group: a combined effect of the HPCS/MP hydrogel and NIR light irradiation; 4) a GEL/DOX group: an effect of the HPCS/MP hydrogel encapsulating DOX·HCL; and 5) a GEL/DOX/LASER group: a combined effect of the HPCS/MP hydrogel encapsulating DOX·HCL and NIR light irradiation. A volume of a hydrogel system was 100 μL, and an amount of the encapsulated DOX·HCL was 10 μg. When the A549 cells were spread to about 90% of a bottom of a cell culture flask, the A549 cells were digested, centrifuged, resuspended, and diluted to 1×10$^6$ cells/mL. 20 μL of a cell suspension was mixed with the hydrogel of the corresponding group as described above. After the cells gelatinized in a water bath of 45° C. for 15 min, 100 μL of fresh medium was added to each well, and then the cells were incubated at 37° C. for 24 h.

After the cells were cultured for 24 h, the cells were taken out and replaced with 100 μL of fresh medium. Then a laser of 808 nm was fixed and adjusted to a right height, and the cells were irradiated for 3 min at a power of 1 W/cm$^2$ per well. The cells were then placed in a 37° C. cell culture incubator and continued to be cultured for 24 h and 48 h and taken out. The cells were fluorescently stained and then photographed under a microscope for observation, and cell viability was detected by a lactate dehydrogenase method.

(1) Results of LDH activity test

Figure 13:
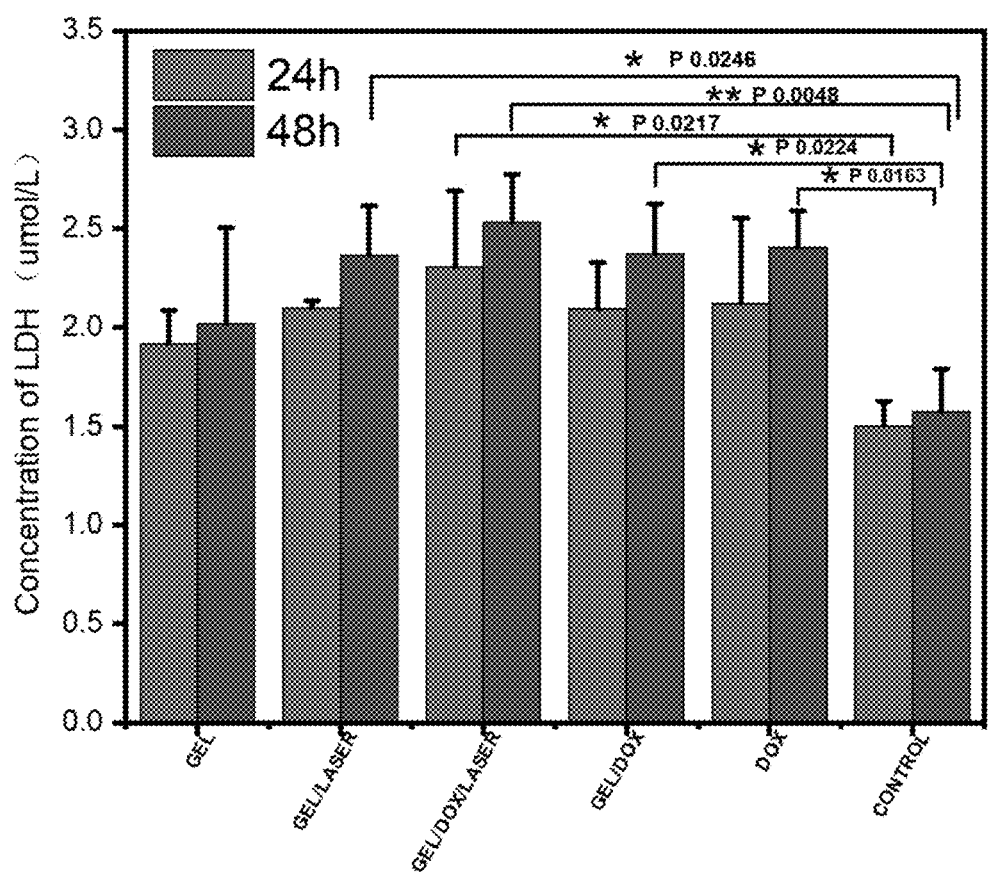
FIG. 13 is a schematic diagram illustrating a lactate dehydrogenase (LDH) release concentration (*$p<0.001$, $p<0.01$, *$p<0.05$) of A549 cells of different treatment groups at 24 h and 48 h according to some embodiments of the present disclosure.

As illustrated in FIG. 13, it can be seen that there was an increase in an LDH activity detected in other treatment groups compared to the Control group, indicating that the growth of the A549 cells was impaired. The result of the GEL/DOX/LASER activity test was about 1.1 times that of GEL/DOX, indicating that the photothermal effect was inhibitory to the A549 cells and capable of killing a part of the A549 cells. The result of the LDH activity test of GEL/DOX/LASER was about 1.09 times that of the GEL/LASER group, indicating that the hydrogel encapsulated DOX·HCL was capable of enhancing the inhibitory effect on tumor cells. In addition, the LDH activity of the GEL/DOX/LASER group was the highest compared to other groups, indicating that more A549 cells were damaged in the GEL/DOX/LASER group, resulting in a release of LDH from cell membranes. This proved that the hydrogel encapsulated DOX and the photothermal effect synergistically inhibited the tumor cells, which is more significantly than when the hydrogel encapsulated DOX and the photothermal effect acted separately, and had a significant difference compared to the control group.

Figure 14:
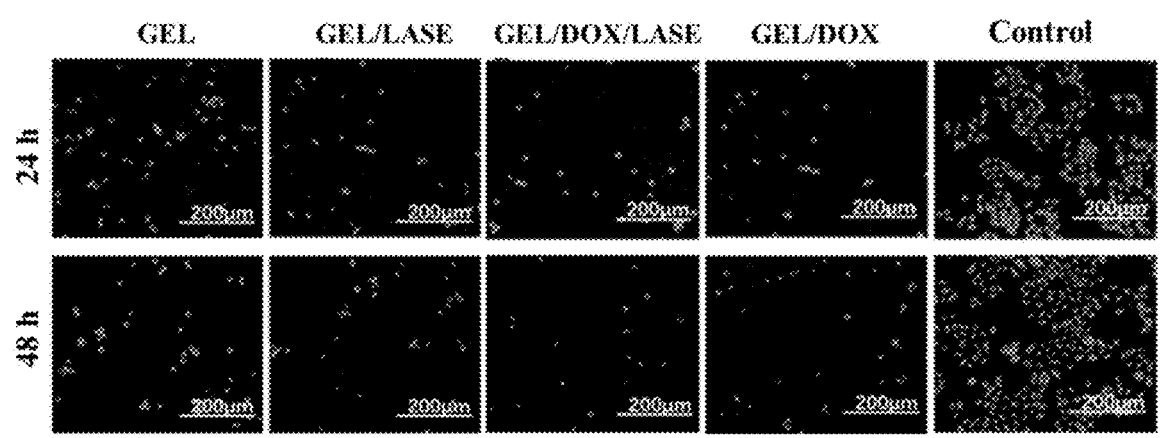
FIG. 14 is a schematic diagram illustrating a growth status (200×; Bar=200 nm) of hydrogel co-cultured A549 cells of different treatment groups at 24 h and 48 h according to some embodiments of the present disclosure.

(2) As illustrated in FIG. 14, compared with the status of the cells in the control group, the growth status of the A549 cells cultured after 24 h and 48 h of incubation in the HPCS/MP hydrogel was poor, forming abnormal round or elliptical morphologies, and sparse distribution of the cells. When the growth status of three-dimensional culturing of the A549 cells in the HPCS/MP hydrogel (GEL group) was compared with the growth status of the cells cultured for 24 and 48 h after encapsulation of DOX·HCL (GEL/DOX group), DOX·HCL had a certain toxic effect on the A549 cells and inhibited the growth of cancer cells, and a count of live cells was significantly reduced.

Meanwhile, the cell growth of the A549 cells co-cultured with GEL/DOX/LASER and GEL/DOX in two groups for 24 and 48 h indicated that the photothermal effect also produced a certain inhibition on the growth of tumor cells. Both chemotherapy and photothermal treatment inhibited the growth of tumor cells when chemotherapy and photothermal treatment acted separately, while the results of the GEL/DOX/MP group showed that the combination of photothermal and chemotherapy was more effective in inhibiting tumor cells.

Figure 15:
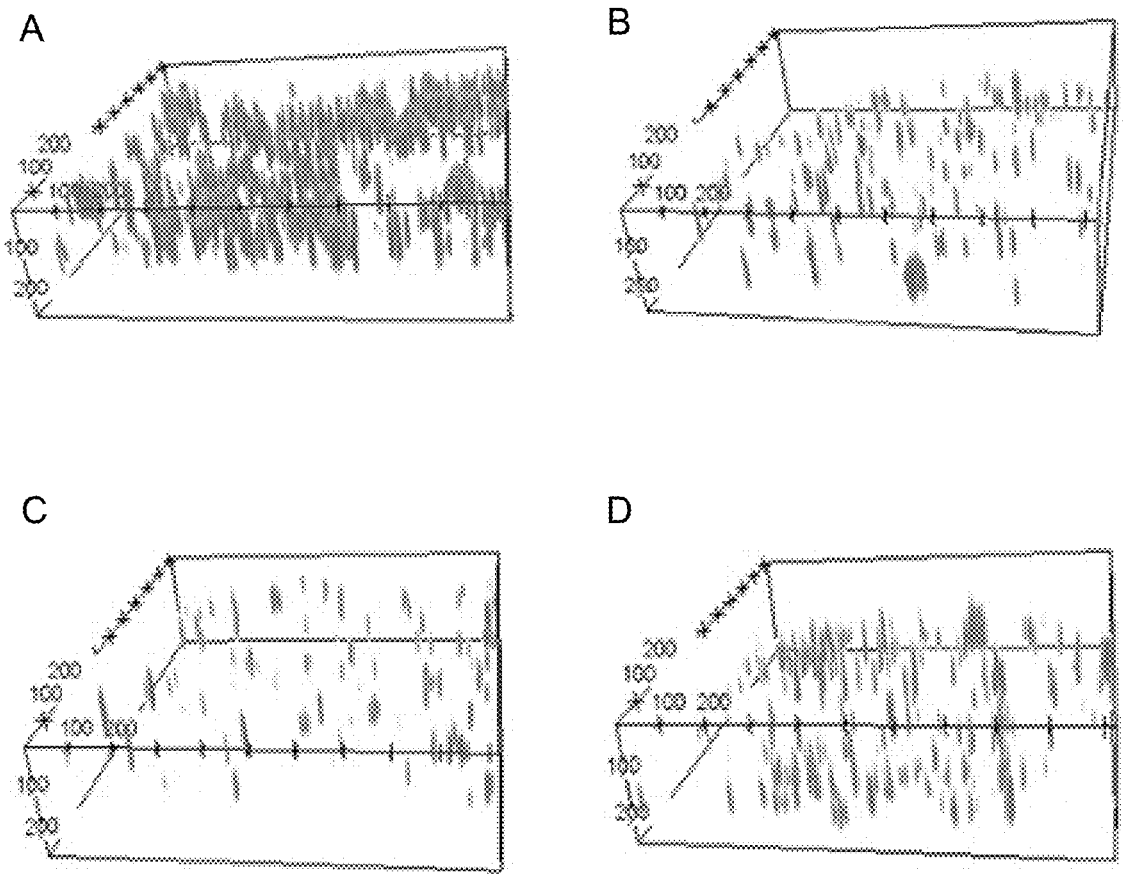
FIG. 15 is a schematic diagram illustrating a growth status (200×; Bar=200 nm) of hydrogel co-cultured A549 cells of different treatment groups for 48 h according to some embodiments of the present disclosure; wherein A is a GEL group, B is a GEL/LASER group, C is a GEL/DOX/LASER group, and D is a GEL/DOX group.

(3) Observation and analysis of the three-dimensional co-culture of the A549 cells in the hydrogel As illustrated in FIG. 15, it can be seen that after the A549 cells were co-cultured in the hydrogel for 48 h, the cells were distributed three-dimensionally in the hydrogel with uniform distribution. It can be seen that the photothermal effect and DOX·HCL separately produced a certain inhibitory effect on the A549 cells, and the count of cells was obviously reduced. The inhibitory effect of the GEL/DOX/LASER photothermal effect and DOX·HCL was the most significant when the GEL/DOX/LASER photothermal effect and DOX·HCL acted synergistically, and the count of live cells was drastically reduced, which indicated that the HPCS/MP hydrogel was applicable to photothermal-chemotherapy combined therapy, and the inhibitory effect of the combined effect was more significant.

Example 4

This Example is directed to in-vivo application experiments with the hydrogel

Thirty female mice were randomly divided into 6 groups with 5 mice per group: (1) a saline group: injection of saline only; (2) a DOX group (5 mg/kg): injection of DOX; (3) a GEL/LASER group: a combined effect of the HPCS/MP hydrogel and NIR light irradiation; (4) a GEL/DOX (5 mg/kg) group: an effect of the HPCS/MP hydrogel encapsulating DOX·HCL; (5) a GEL/DOX (5 mg/kg)/LASER group: a combined effect of HPCS/MP hydrogel encapsulating DOX·HCL and NIR light irradiation, and (6) an indocyanine green (ICG) (1 mg/kg) group: injection of ICG. The different groups of mice were injected with 100 μL of saline, DOX, ICG, an HPCS/MP hydrogel precursor solution, and a GEL/DOX hydrogel precursor solution by intratumoral injection.

In the laser irradiation group LASER was irradiated for 5 min using an laser of 808 nm at a power of 1 W/cm$^2$ on days 2, 4, 6, 8, 10, and 12 after drug administration, and an irradiated site was a tumor site visible to naked eyes, with a light source positioned 5 cm from a body surface. The date of irradiation was designated as day 1, and an observation period extended to 14 days. A tumor volume was measured with a vernier caliper and a weight of the mice was weighed using an electronic balance every two days, and then a curve of the tumor volume, the body weight, and time was plotted. On the 14th day, the mice were euthanized, and axillary tumor bodies and tissues of the heart, liver, spleen, lung, and kidney of the mice were collected. The weights of the tumors and organ tissues of the various groups were accurately measured and recorded to calculate a tumor inhibition rate and an organ index of each group. Then immunohistochemistry and HE staining were performed for pathological analysis.

Results analysis is as follows.

1. In-Vivo Photothermal Conversion Effect

Figure 16:
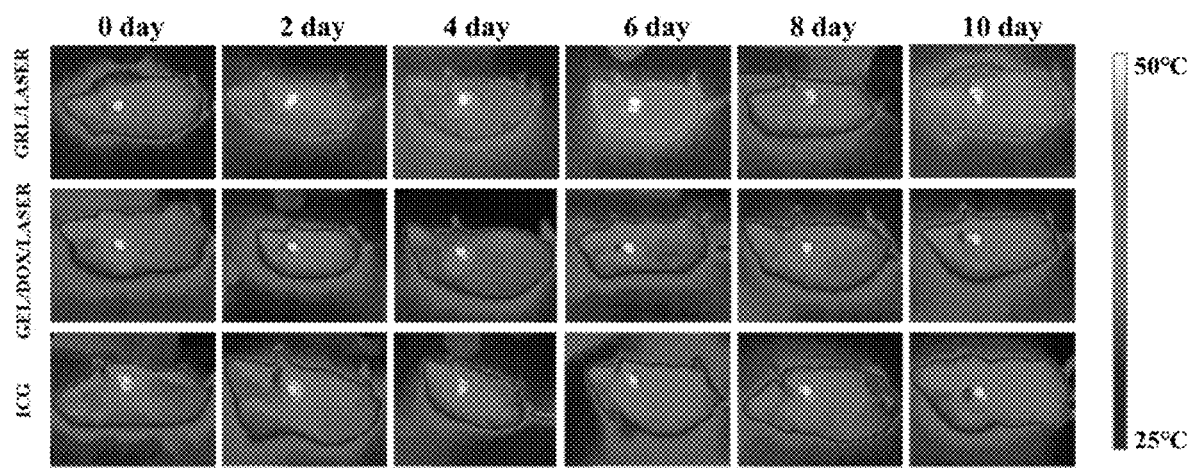
FIG. 16 is a schematic diagram illustrating an infrared thermogram of photothermal heating of a mouse tumor site according to some embodiments of the present disclosure.

A temperature change at the tumor site was recorded using an infrared camera. As illustrated in FIG. 16, when irradiated with 808 nm NIR light, both the GEL/LASER group and the GEL/DOX/LASER group reached a maximum temperature of 50° C. within 5 min; the ICG group reached a maximum temperature of about 45° C. within 5 min of irradiation. All three light irradiation groups reached an effective tumor cell thermal ablation temperature and a hydrogel formation temperature. Thereafter, in the course of the treatment, light irradiation was performed for 5 min every 48 h until the end of the treatment on the 14th day.

2. Analysis of Relative Changes in Body Weights of Mice

Figure 17:
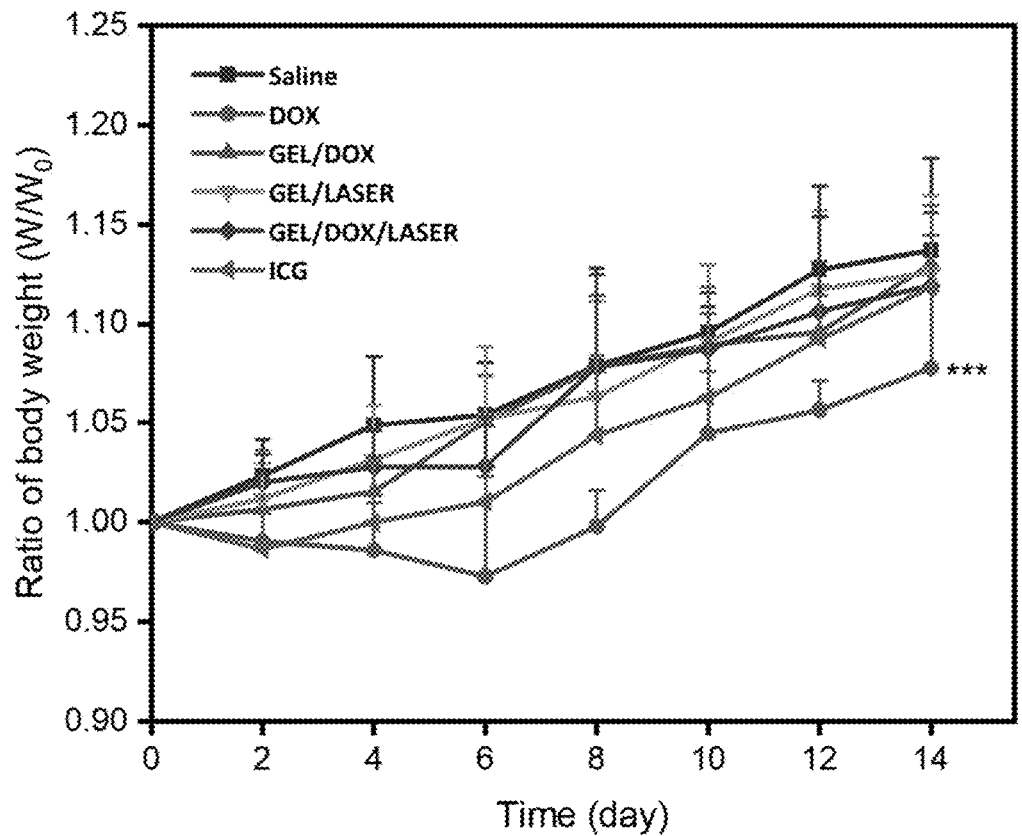
FIG. 17 is a schematic diagram illustrating a change in relative body weights of six groups of mice according to some embodiments of the present disclosure.

As illustrated in FIG. 17, the overall body weights of the mice in the control group and the five treatment groups showed an increase trend. The GEL/DOX/LASER group showed a slower increase in the body weight in the 6 days following the start of treatment. The DOX group showed a significant downward trend in the body weight in the 6 days of treatment, followed by a slow increase. The GEL/DOX group showed a significant increase trend in the body weight compared to the DOX group. The ICG group showed a decrease trend in the body weight during the first 2 days of treatment, which then improved, and the body weight began to gradually increase. The above indicated that ICG and DOX·HCL had different degrees of toxic effects on the mice, which were unfavorable to the normal growth of the mice. Hydrogel encapsulated DOX·HCL was capable of effectively alleviating the toxic effects of DOX·HCL.

3. Observation on Organ Indices and Histopathology in Mice

Figure 18:
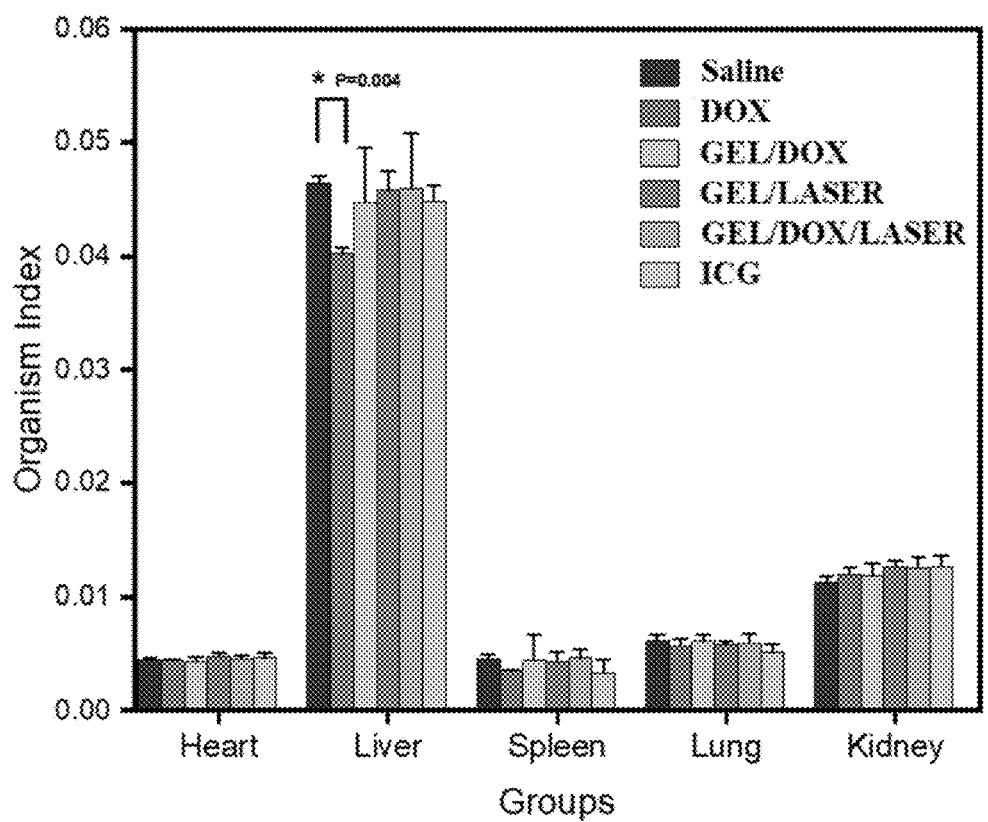
FIG. 18 is a schematic diagram illustrating an organ index (*$p<0.001$, $p<0.01$, *$p<0.05$) of six groups of mice according to some embodiments of the present disclosure.

As illustrated in FIG. 18, there were no significant differences in the cardiac, splenic, pulmonary, or renal indices in the individual treatment groups compared to the control group. However, the liver index was significantly reduced in the DOX group compared to the liver index of the control group, indicating that DOX·HCL produced toxic effects on normal organ tissues.

Figure 19:
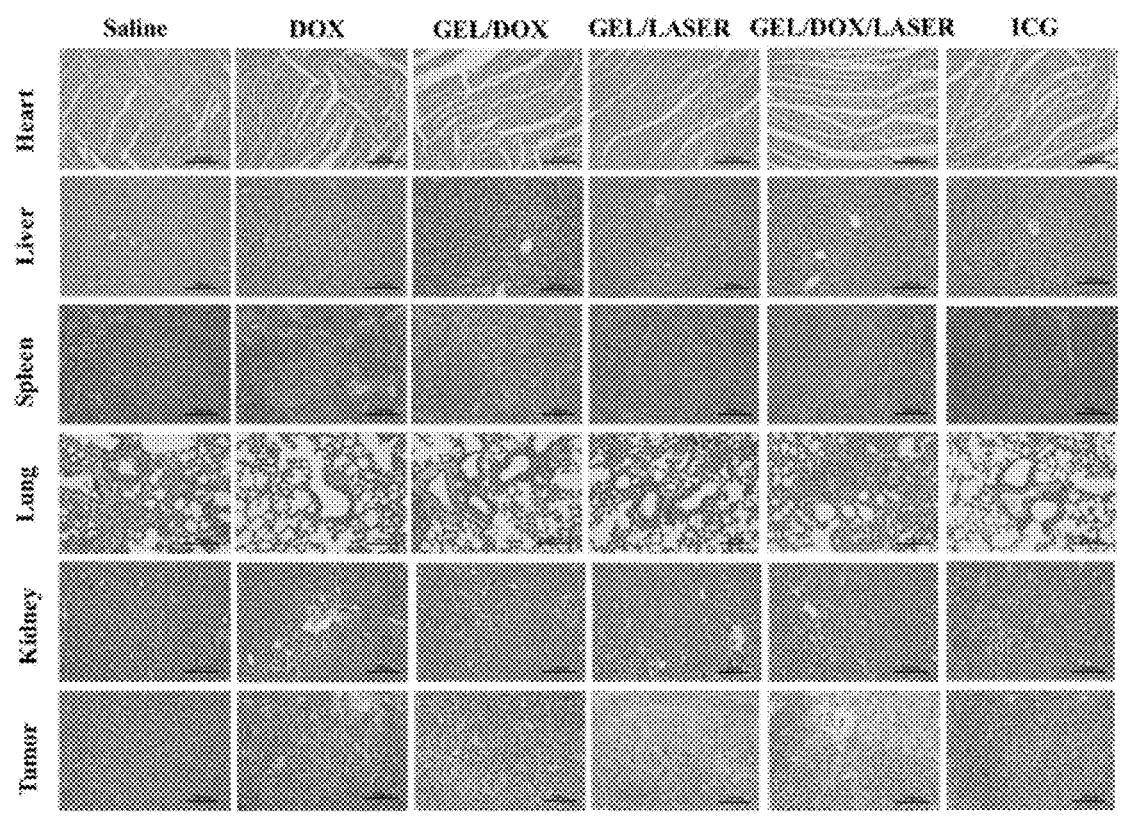
FIG. 19 is a schematic diagram illustrating a result (200×; Bar=200 nm) of HE staining of organ tissues from six groups of mice according to some embodiments of the present disclosure.

As illustrated in FIG. 19, the myocardial fibers of the six groups of mice were neatly aligned with obvious transverse striations, and did not show any obvious necrotic or inflammatory reactions. Staining results of liver sections showed that compared with the control group, the liver tissues of the DOX and GEL/DOX groups became very loose, and the spacing between the cells became larger, while the liver tissues of the GEL/LASER, GEL/DOX/LASER, and ICG groups also showed a slight loosening, and the spacing between the cells became slightly larger.

It can be seen from the staining results of the spleen tissues that compared with the control group, the cell spacing of the DOX group became larger, and the tissues became loose, and the remaining four groups also showed a slight damage. Similarly, the lung tissues in the DOX group showed some degree of damage, with alveolar breakage and dilatation, while the remaining groups showed a relatively slight damage.

The results of renal tissue sections showed that DOX·HCL also had some slight damage to the kidney, with loosely arranged cells and the appearance of obvious degenerated vacuoles. It can be evidently seen from the staining results of the tumor tissues of each group that compared with the untreated control group, the treatment of each treatment group had a certain destructive effect on the tumor tissues, but the destructive effect of the GEL/DOX/LASER group was the most obvious, and the arrangement of the tumor tissues became very loose, indicating that the GEL/DOX/LASER group had the strongest destructive and inhibitory effect on the tumor tissues, and the therapeutic effect was better.

4. Analysis of Changes in Tumor Index in Mice

Figure 20:
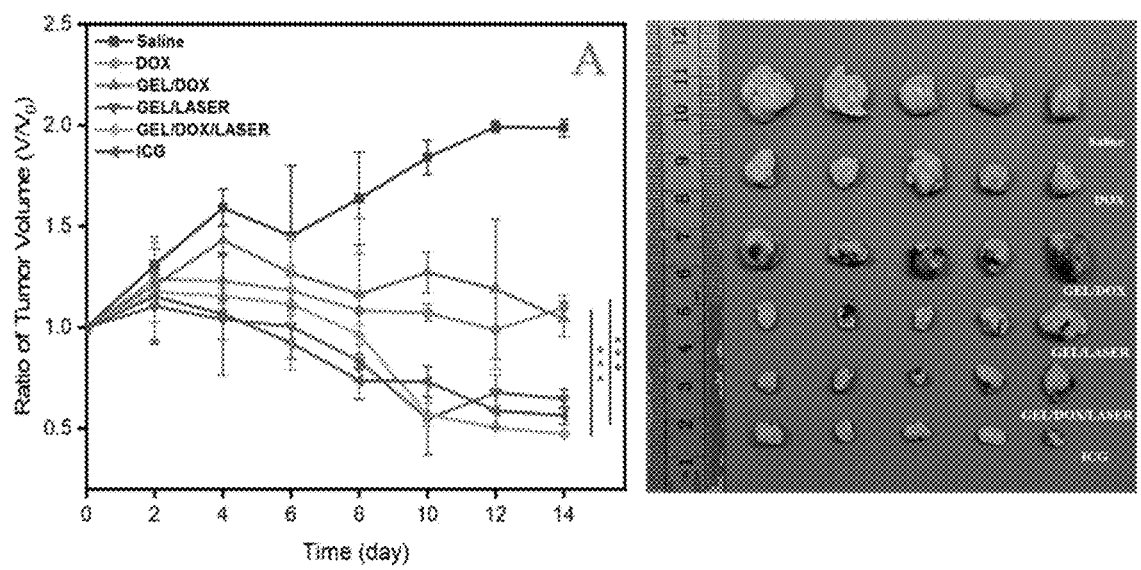
FIG. 20 is a schematic diagram illustrating a tumor change in six groups of mice according to some embodiments of the present disclosure; wherein A is a schematic diagram illustrating a change in a tumor volume with treatment time, and B is a schematic diagram illustrating a picture (*$p<0.001$, $p<0.01$, *$p<0.05$) of tumors in each treatment group on the 14th day of the treatment.

A change in the tumor volume over treatment time was illustrated in FIG. 20, with the control group showing the most pronounced increase in the tumor volume and the GEL/DOX group showing a sustained decrease in the tumor volume, which reflected a good slow-release effect of the drug-carrying hydrogel. Meanwhile, under the combined effect of photothermal and chemotherapeutic treatment, the inhibitory effect on tumors was significantly enhanced, showing a significant difference compared with the control group. The significant difference in the tumor volume between the GEL/DOX group, the GEL/LASER group, and the GEL/DOX/LASER group indicated that the therapeutic effect of the photothermal-chemotherapy combined action was better than that when the photothermal treatment and chemotherapy acted separately.

Figure 21:
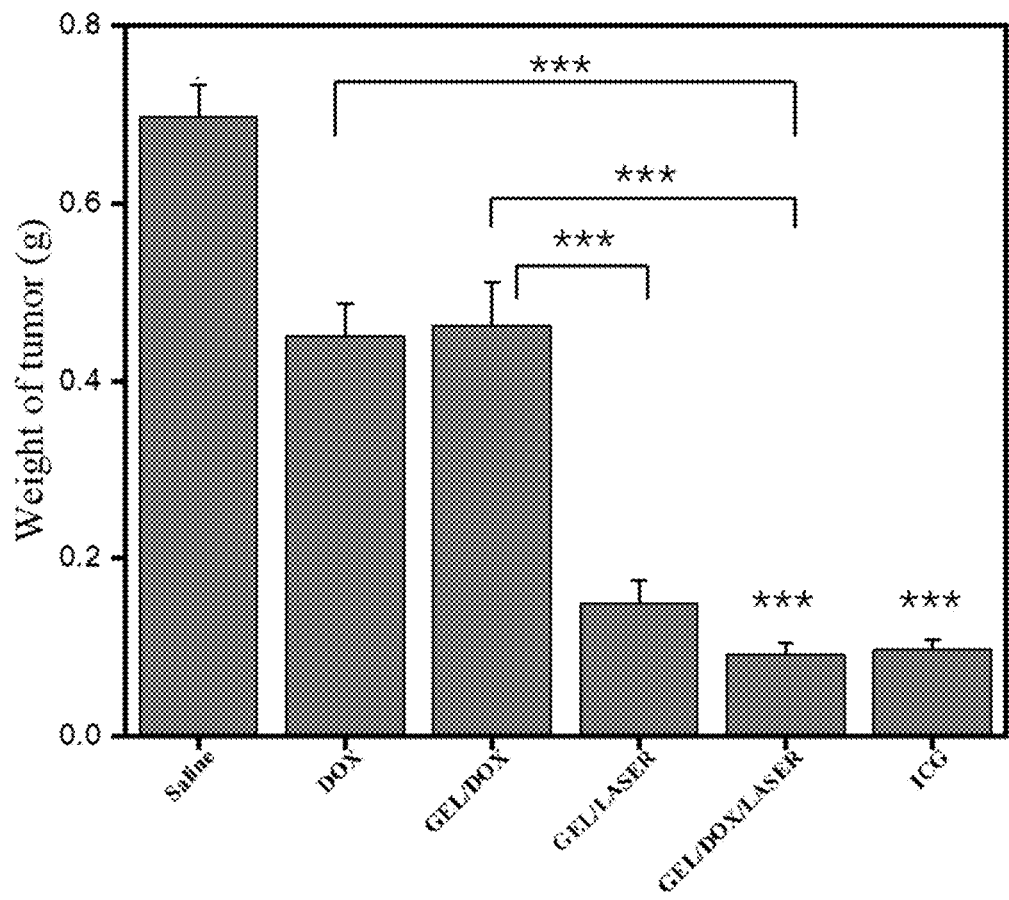
FIG. 21 is a schematic diagram illustrating an average tumor weight (*$p<0.001$, $p<0.01$, *$p<0.05$) of six groups of mice according to some embodiments of the present disclosure.

As illustrated in FIG. 21, the most significant therapeutic effect of photothermal-chemotherapy combined treatment was achieved in the GEL/DOX/LASER group, and the tumor inhibition rate was calculated to be 87% after 14 days of treatment.

5. Immunohistochemical Analysis of Mouse Tumor Tissues

Figure 22:
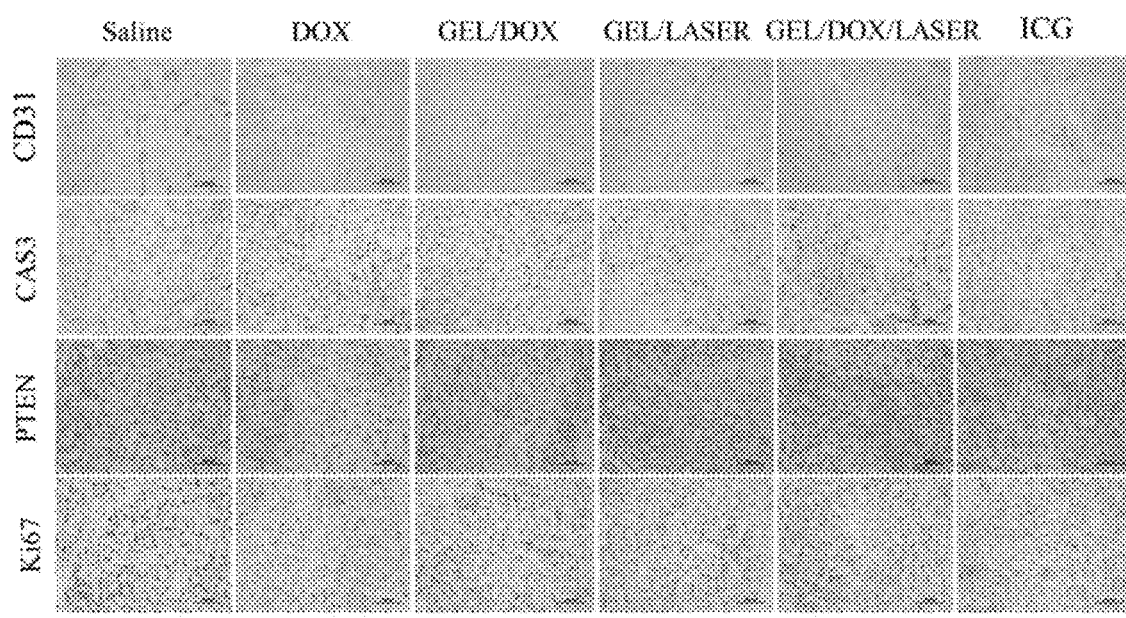
FIG. 22 is a schematic diagram illustrating immunohistochemical analysis of tumor tissues from six groups of mice according to some embodiments of the present disclosure.
Figure 23:
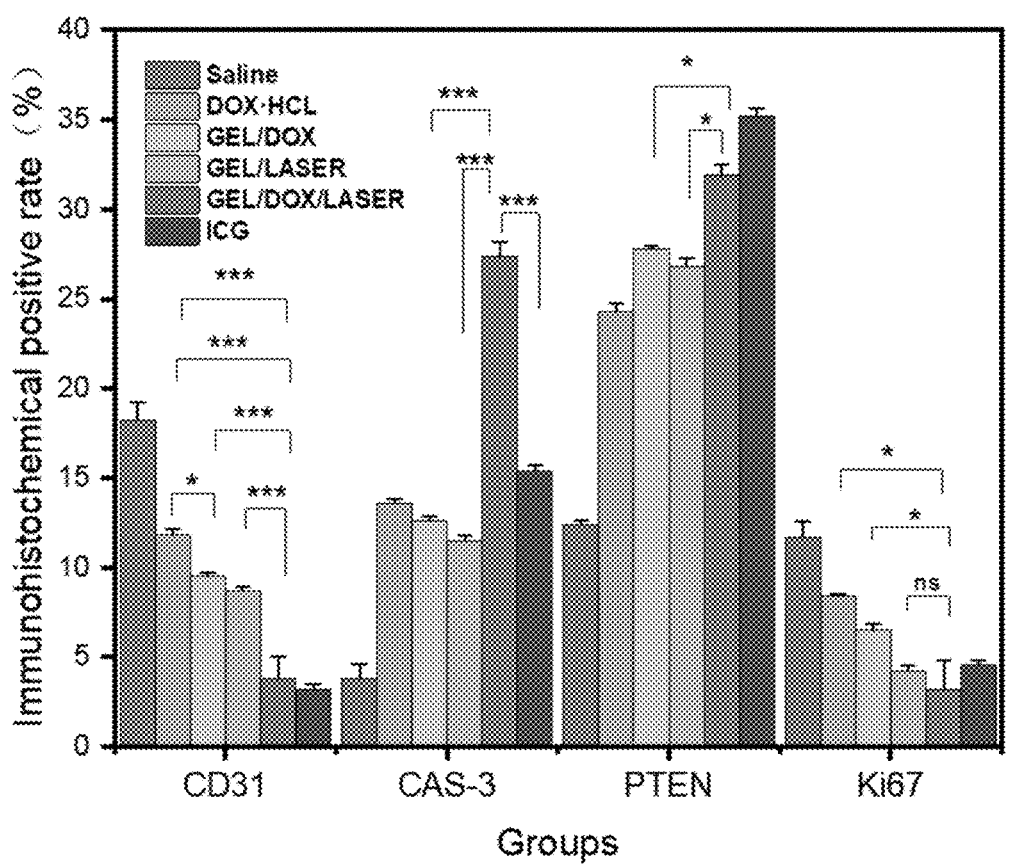
FIG. 23 is a schematic diagram illustrating a result (*$p<0.001$, $p<0.01$, *$p<0.05$) of an immunohistochemistry positivity rate according to some embodiments of the present disclosure.

Tumor tissues from each group of mice were embedded and sliced, and then subjected to immunohistochemical analysis of Ki67, CD31, cysteine asparaginase-3 (Caspase-3), and PTEN, respectively. As illustrated in FIG. 22, it can be seen that the Saline group expressed significantly more CD31 positive substances than other groups, indicating that there was tumor angiogenesis in the Saline group. The results of the positive rate analysis of FIG. 23 further indicated that the Saline group had the highest CD31-positive expression rate in the tumor tissues, indicating that all the treatment groups showed a certain effect of tumor growth inhibition. The CD31 expression rate in the GEL/DOX and GEL/LASER groups was about 3.1 and 2.5 times higher than that in the GEL/DOX/LASER group, indicating that the synergistic effect of the photothermal-chemotherapy combined treatment was more significant than the effect when the photothermal treatment and chemotherapy act separately.

Caspase-3 in the tumor tissues of the Saline group was less expressed compared with the treatment groups, and basically no brownish-yellow particles were observed. The highest rate of Caspase-3 positive expression was found in the GEL/DOX/LASER group among the treatment groups, which was about 2.2 and 2.4 times higher than that of the GEL/DOX and GEL/LASER groups, and also significantly higher than that in the ICG group, indicating that the GEL/DOX/LASER group had a better inhibitory effect on the growth and proliferation of the tumor tissues.

The Saline group had less PTEN expression, fewer brownish-yellow particles than the treatment groups, and a lighter color. The PTEN positive expression rate of each treatment group was significantly higher than that of the Saline group, indicating that each treatment group was capable of preventing the growth of tumor cells. The PTEN positive expression rate in the GEL/DOX/LASER group was about 2.7 times higher than that in the Saline group, indicating that the synergistic effect of the photothermal-chemotherapy combined treatment was significant.

There was more Ki67-positive material in the Saline group, indicating faster tumor growth in the Saline group, while there was less Ki67 expression in the treatment groups. The GEL/DOX/LASER group had the lowest positive expression rate in the tumor tissues, indicating that the inhibition of tumor tissues was more significant in the GEL/DOX/LASER group.

The HPCS/DOX/MP hydrogel prepared by the present disclosure has a good photothermal conversion effect, with a high conversion efficiency of about 41%. Applying the HPCS/DOX/MP hydrogel to the photothermal-chemotherapy combined treatment has a better inhibition effect on tumor cells. The in-vivo tumor inhibition effect of the combination treatment is explored by establishing an LA795 lung adenocarcinoma mouse tumor model, and reveals that the photothermal-chemotherapy combined treatment has a better inhibitory effect on the tumor, and the tumor inhibition rate can reach 87% after 14 days, which is comparable to that of the positive control group, and causes less damage to normal organ tissues.

The basic concept has been described above. Obviously, for those skilled in the art, the above detailed disclosure is only an example, and does not constitute a limitation to the present disclosure. Although not expressly stated here, those skilled in the art may make various modifications, improvements and corrections to the present disclosure. Such modifications, improvements and corrections are suggested in this disclosure, so such modifications, improvements and corrections still belong to the spirit and scope of the exemplary embodiments of the present disclosure.

Meanwhile, the present disclosure uses specific words to describe the embodiments of the present disclosure. For example, "one embodiment", "an embodiment", and/or "some embodiments" refer to a certain feature, structure or characteristic related to at least one embodiment of the present disclosure. Therefore, it should be emphasized and noted that references to "one embodiment" or "an embodiment" or "an alternative embodiment" two or more times in different places in the present disclosure do not necessarily refer to the same embodiment. In addition, certain features, structures or characteristics in one or more embodiments of the present disclosure may be properly combined.

In addition, unless clearly stated in the claims, the sequence of processing elements and sequences described in the present disclosure, the use of counts and letters, or the use of other names are not used to limit the sequence of processes and methods in the present disclosure. While the foregoing disclosure has discussed by way of various examples some embodiments of the invention that are presently believed to be useful, it should be understood that such detail is for illustrative purposes only and that the appended claims are not limited to the disclosed embodiments, but rather, the claims are intended to cover all modifications and equivalent combinations that fall within the spirit and scope of the embodiments of the present disclosure. For example, although the implementation of various components described above may be embodied in a hardware device, it may also be implemented as a software only solution, e.g., an installation on an existing server or mobile device.

In the same way, it should be noted that in order to simplify the expression disclosed in this disclosure and help the understanding of one or more embodiments of the invention, in the foregoing description of the embodiments of the present disclosure, sometimes multiple features are combined into one embodiment, drawings or descriptions thereof. This method of disclosure does not, however, imply that the subject matter of the disclosure requires more features than are recited in the claims. Rather, claimed subject matter may lie in less than all features of a single foregoing disclosed embodiment.

In some embodiments, counts describing the quantity of components and attributes are used. It should be understood that such counts used in the description of the embodiments use the modifiers "about", "approximately" or "substantially" in some examples. Unless otherwise stated, "about", "approximately" or "substantially" indicates that the stated figure allows for a variation of +20%. Accordingly, in some embodiments, the numerical parameters used in the disclosure and claims are approximations that can vary depending upon the desired characteristics of individual embodiments. In some embodiments, numerical parameters should consider the specified significant digits and adopt the general digit retention method. Although the numerical ranges and parameters used in some embodiments of the present disclosure to confirm the breadth of the range are approximations, in specific embodiments, such numerical values are set as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. An injectable photothermal hydrogel based on melanin, wherein the injectable photothermal hydrogel is a hydroxypropyl chitosan/bis-amino polyethylene glycol modified melanin nanoparticles (HPCS/MP) hydrogel, the HPCS/MP hydrogel is prepared by mixing bis-amino polyethylene glycol modified melanin nanoparticles (MP) with hydroxypropyl chitosan (HPCS); the MP is synthesized by an amidation reaction of melanin and bis-amino PEG; a ratio of a volume of an MP solution to a volume of an HPCS solution in the HPCS/MP hydrogel is 4:6; and a concentration of the MP solution is 20 wt %, and a concentration of the HPCS solution is 4 wt %.

2. The injectable photothermal hydrogel of claim 1, wherein the HPCS/MP hydrogel has a tight surface structure, the HPCS/MP hydrogel has a void structure, and a hydrogen bond cross-linking reaction is formed within hydrogel molecules of the HPCS/MP hydrogel, such that the HPCS/MP hydrogel is injectable.

3. The injectable photothermal hydrogel of claim 1, wherein the HPCS/MP hydrogel maintains a stability at 37°

C. or a gelation temperature of 43° C.; an encapsulation efficiency of the HPCS/MP hydrogel is 90%+3%; an encapsulated drug from the HPCS/MP hydrogel is more conducive to be released under an acidic environment, and a controlled release of the encapsulated drug from the HPCS/MP hydrogel is achieved through an external laser.

4. The injectable photothermal hydrogel of claim 1, wherein the melanin is natural melanin.

5. The injectable photothermal hydrogel of claim 4, wherein the melanin is extracted from cuttlefish.

6. A preparation method of an injectable photothermal hydrogel based on melanin of claim 1, comprising:
   (1) preparing MP, including steps of: dissolving $NH_2$-PEG-$NH_2$ in a Tris buffer solution; ultrasonically dispersing melanin in the Tris buffer solution, then adding 1-(3-dimethylaminopropyl)-3-ethylcarbodiimide hydro (EDC) and N-hydroxysuccinimide (NHS), and stirring; dropwise adding a $NH_2$-PEG-$NH_2$ solution into a melanin solution and stirring to obtain a mixed reaction solution; and dehydrating and removing impurities from the mixed reaction solution with absolute ethanol, and freeze-drying to obtain the MP;
   (2) preparing HPCS, including steps of: adding chitosan powder into a NaOH solution to fully swell the chitosan, then adding isopropyl alcohol, stirring, adding propylene oxide, and heating in a water bath for reaction; removing impurities, and then dissolving in deionized water to adjust a pH to neutral; and obtaining the HPCS after dialysis and freeze-drying;
   (3) preparing an MP solution and an HPCS solution; and
   (4) evenly mixing the MP solution and the HPCS solution to obtain the HPCS/MP hydrogel.

\* \* \* \* \*